(12) United States Patent
Shih et al.

(10) Patent No.: US 8,481,335 B2
(45) Date of Patent: Jul. 9, 2013

(54) SPECIFICITY AND SENSITIVITY ENHANCEMENT IN CANTILEVER SENSING

(75) Inventors: Wei-Heng Shih, Bryn Mawr, PA (US); Wan Y. Shih, Bryn Mawr, PA (US)

(73) Assignee: Drexel University, Philadelphia, PA (US)

( * ) Notice: Subject to any disclaimer, the term of this patent is extended or adjusted under 35 U.S.C. 154(b) by 545 days.

(21) Appl. No.: 12/677,613

(22) PCT Filed: Oct. 3, 2008

(86) PCT No.: PCT/US2008/078675
§ 371 (c)(1),
(2), (4) Date: Mar. 11, 2010

(87) PCT Pub. No.: WO2009/046251
PCT Pub. Date: Apr. 9, 2009

(65) Prior Publication Data
US 2010/0210032 A1    Aug. 19, 2010

Related U.S. Application Data

(63) Continuation-in-part of application No. 11/943,790, filed on Nov. 21, 2007.

(60) Provisional application No. 60/867,245, filed on Nov. 27, 2006, provisional application No. 60/977,776, filed on Oct. 5, 2007, provisional application No. 61/046,899, filed on Apr. 22, 2008.

(51) Int. Cl.
*G01N 33/551* (2006.01)

(52) U.S. Cl.
USPC ... 436/524; 310/311; 310/313 R; 310/323.21; 435/287.2; 436/525; 436/527

(58) Field of Classification Search
None
See application file for complete search history.

(56) References Cited

U.S. PATENT DOCUMENTS

| 3,205,464 A | 9/1965 | Schwartz |
| 4,093,883 A | 6/1978 | Yamamoto |
| 4,302,694 A | 11/1981 | Fujishima et al. |
| 4,349,762 A | 9/1982 | Kitamura et al. |

(Continued)

FOREIGN PATENT DOCUMENTS

| EP | 0631319 A1 | 12/1994 |
| EP | 1536227 A2 | 6/2005 |

(Continued)

OTHER PUBLICATIONS

Rijal, et al., "Method for measuring the Self-Assembly of Alkanethiols on Gold at Femtomolar Concentrations," Langmuir, 23, 6856-6863 (2007).

(Continued)

*Primary Examiner* — Chris L Chin
(74) *Attorney, Agent, or Firm* — Mendelsohn, Drucker & Associates, P.C.

(57) ABSTRACT

The invention is directed to a sensor system including at least one sensor and target specific receptors bound substrates for purposes of enhancing detection sensitivity. Optionally, the sensor system may include quantum dots for independently verifying the presence of a target molecule or compound. The sensor system may be particularly beneficial in the field of medical diagnostics, bio-defense, food safety, water safety and general chemical detection.

10 Claims, 13 Drawing Sheets

U.S. PATENT DOCUMENTS

| | | | |
|---|---|---|---|
| 4,363,993 A | 12/1982 | Nishigaki et al. | |
| 4,528,502 A | 7/1985 | Rocha | |
| 4,649,312 A | 3/1987 | Robin et al. | |
| 4,802,371 A | 2/1989 | Calderara et al. | |
| 5,054,323 A | 10/1991 | Hubbard et al. | |
| 5,313,535 A | 5/1994 | Williams | |
| 5,334,835 A | 8/1994 | Nakayama et al. | |
| 5,338,999 A | 8/1994 | Ramakrishnan et al. | |
| 5,382,864 A | 1/1995 | Morikawa et al. | |
| 5,445,008 A | 8/1995 | Wachter et al. | |
| 5,475,318 A | 12/1995 | Marcus et al. | |
| 5,501,986 A * | 3/1996 | Ward et al. | 436/525 |
| 5,503,010 A | 4/1996 | Yamanaka | |
| 5,553,486 A | 9/1996 | Bonin | |
| 5,626,728 A | 5/1997 | Ramakrishnan et al. | |
| 5,689,063 A | 11/1997 | Fujiu et al. | |
| 5,719,324 A | 2/1998 | Thundat et al. | |
| 5,780,727 A | 7/1998 | Gimzewski et al. | |
| 5,807,758 A * | 9/1998 | Lee et al. | 436/526 |
| 5,866,807 A | 2/1999 | Elings et al. | |
| 5,874,126 A | 2/1999 | Kahn et al. | |
| 5,948,993 A | 9/1999 | Ting et al. | |
| 5,966,787 A | 10/1999 | Nakayama et al. | |
| 5,996,412 A | 12/1999 | Hansen | |
| 6,075,585 A | 6/2000 | Minne et al. | |
| 6,278,379 B1 | 8/2001 | Allen et al. | |
| 6,280,396 B1 | 8/2001 | Clark | |
| 6,289,717 B1 | 9/2001 | Thundat et al. | |
| 6,336,366 B1 | 1/2002 | Thundat et al. | |
| 6,422,069 B1 | 7/2002 | Shimizu et al. | |
| 6,458,327 B1 | 10/2002 | Vossmeyer | |
| 6,465,368 B2 | 10/2002 | Inoue et al. | |
| 6,579,726 B1 * | 6/2003 | Natan et al. | 436/518 |
| 6,589,727 B1 | 7/2003 | Klenerman et al. | |
| 6,621,080 B2 | 9/2003 | Yamamoto | |
| 6,734,425 B2 | 5/2004 | Hantschel et al. | |
| 6,781,285 B1 | 8/2004 | Lazarus et al. | |
| 6,903,491 B2 | 6/2005 | Irie et al. | |
| 6,992,421 B2 | 1/2006 | Ikeda et al. | |
| 7,055,378 B2 | 6/2006 | Su et al. | |
| 7,083,270 B2 | 8/2006 | Torii et al. | |
| 7,084,554 B2 | 8/2006 | Xu et al. | |
| 7,104,134 B2 | 9/2006 | Amano et al. | |
| 7,195,909 B2 | 3/2007 | Klenerman et al. | |
| 7,263,874 B2 | 9/2007 | Fitch et al. | |
| 7,335,345 B2 | 2/2008 | Shih et al. | |
| 7,458,265 B2 | 12/2008 | Shih et al. | |
| 7,497,133 B2 | 3/2009 | Shih et al. | |
| 7,597,870 B2 | 10/2009 | Shih et al. | |
| 7,744,773 B2 | 6/2010 | Shih et al. | |
| 7,942,056 B2 | 5/2011 | Mutharasan et al. | |
| 7,992,431 B2 | 8/2011 | Shih et al. | |
| 2002/0094528 A1 | 7/2002 | Salafsky | |
| 2002/0117659 A1 | 8/2002 | Lieber et al. | |
| 2002/0155303 A1 | 10/2002 | Wielstra et al. | |
| 2003/0032293 A1 | 2/2003 | Kim et al. | |
| 2003/0068655 A1 | 4/2003 | Bottomley et al. | |
| 2003/0194697 A1 | 10/2003 | Klenerman et al. | |
| 2003/0224551 A1 | 12/2003 | Kim et al. | |
| 2003/0235681 A1 | 12/2003 | Sebastian et al. | |
| 2004/0022677 A1 | 2/2004 | Wohlstadter et al. | |
| 2004/0265664 A1 | 12/2004 | Badding et al. | |
| 2005/0112621 A1 | 5/2005 | Kim et al. | |
| 2005/0114045 A1 | 5/2005 | Giurgiutiu et al. | |
| 2005/0199047 A1 | 9/2005 | Adams et al. | |
| 2005/0277852 A1 | 12/2005 | Shih et al. | |
| 2005/0287680 A1 | 12/2005 | Venkatasubbarao et al. | |
| 2006/0053870 A1 | 3/2006 | Berndt | |
| 2006/0217893 A1 | 9/2006 | Li et al. | |
| 2006/0223691 A1 | 10/2006 | Shih et al. | |
| 2006/0228657 A1 | 10/2006 | Masters et al. | |
| 2006/0257286 A1 | 11/2006 | Adams | |
| 2007/0089515 A1 | 4/2007 | Shih et al. | |
| 2007/0141721 A1 | 6/2007 | Vafai et al. | |
| 2007/0169553 A1 | 7/2007 | Mutharasan | |
| 2007/0218534 A1 | 9/2007 | Klenerman et al. | |
| 2008/0034840 A1 | 2/2008 | Mutharasan | |
| 2008/0035180 A1 | 2/2008 | Mutharasan | |
| 2009/0007645 A1 | 1/2009 | Shih et al. | |
| 2009/0053709 A1 | 2/2009 | Mutharasan | |
| 2009/0065742 A1 | 3/2009 | Shih et al. | |
| 2009/0078023 A1 | 3/2009 | Mutharasan | |
| 2009/0203000 A1 | 8/2009 | Mutharasan | |
| 2010/0068697 A1 | 3/2010 | Shih et al. | |
| 2010/0239463 A1 | 9/2010 | Shih et al. | |

FOREIGN PATENT DOCUMENTS

| | | |
|---|---|---|
| JP | 3093849 B2 | 4/2000 |
| JP | 2003-298131 A | 10/2003 |
| JP | 2004-265899 A | 9/2004 |
| JP | 2007-67125 A | 3/2007 |
| WO | 98/50773 A2 | 11/1998 |
| WO | 2004/061991 A1 | 7/2004 |
| WO | 2005/043126 A2 | 5/2005 |
| WO | 2006/031072 A1 | 3/2006 |
| WO | 2007/087328 A2 | 8/2007 |
| WO | 2007/133619 A1 | 11/2007 |
| WO | 2008/020903 A2 | 2/2008 |
| WO | 2008/021187 A2 | 2/2008 |
| WO | 2008/021189 A2 | 2/2008 |
| WO | 2008/101199 A1 | 8/2008 |
| WO | 2009/014830 A1 | 1/2009 |
| WO | 2009/035732 A2 | 3/2009 |
| WO | 2009/035732 A3 | 3/2009 |
| WO | 2009/046251 A2 | 4/2009 |

OTHER PUBLICATIONS

Wilson, et al., "Viscosity and density values from excitation level response of piezoelectric-excited cantilever sensors," Sensors and Actuators A 138, 44-51 (2007).

Gu, et al., "Single-Calcination Synthesis of Pyrochlore-Free 0.9Pb (Mg1/3Nb2/3)O3-0.1PbTiO3 and Pb(Mg1/3Nb2/3) O3 Ceramics using a Coating Method," J. Am. Ceram. Soc., 86 [2] 217-21 (2003).

Thaysen, et al., "Cantilever-Based Bio-Chemical Sensor Integrated in a Microliquid Handling System," 401-404 (2001).

Li, et al., Micromachined Biomimetic Sensor Using a Modular Artificial Hair Cells, pp. 1-3.

Thaysen, "Label free Detection, BioMEMs Materials and Fabrication Methods," Track 2, 3:00pm, pp. 1-3, Sep. 7, 2002.

Written Opinion of the International Searching Authority, PCT/US2008/078675 (Oct. 3, 2008).

X. Li, W.Y. Shih, J. S. Vartuli, D. L. Milius, I. A. Aksay, and W.-H. Shih, "Effect of Transverse Tensile Stress on Electric-Field-Induced Domain Reorientation in Soft PZT: In Situ XRD Study", J. Am. Ceram. Soc. 85 (4), 844 (2002).

H. Zhang, et al., "A Sensitive and High-Throughput Assay to Detect Low-Abundance Proteins in Serum," Nature Medicine 12(4) 473-477 (2006).

J.-W. Park, S. Kurosawa, H. Aizawa Y. Goda, M. Takai and K. Ishihara, "Piezoelectric Immunosensor for Bisphenol A Based on Signal Enhancing Step With 2-methacrolyloxyethyl Phosphorylcholine Polymeric Nanoparticle," Analyst, 131, 155-162 (2006).

A. M. Smith, G. Ruan, M. N. Rhyner, and S. Nie, "Engineering Luminescent Quantum Dots for In Vivo Molecular and Cellular Imaging," Ann. Biomed. Eng., 34 (1),3-14 (2006).

R. E. Jaeger and L. Egerton, "Hot-Pressing of Potassium-Sodium Niobates," J. Am. Ceram. Soc. 45, 209 (1962).

H. Birol, D. Damjanovic and N. Setter, "Preparation and Characterization of (K0.5Na0.5)NbO3 Ceramics", J. Eur. Ceram. Soc. 26, 861 (2006).

Y. Guo, K. Kakimoto, and H. Ohsato, "Phase Transitional Behavior and Piezoelectric Properties of (Na0.5K0.5)NbO3-LiNbO3 Ceramics," Appl. Phys. Lett., 85, 4121 (2004).

Y. Guo, K. Kakimoto, and H. Ohsato, "(Na0.5K0.5)NbO3-LiTaO3 Lead-free Piezoelectric Ceramics," Mater. Lett., 59, 241 (2005).

H. Li, W.Y. Shih, and W.-H. Shih, "Effect of Antimony Concentration on the Crystalline Structure, Dielectric and Piezoelectric Properties of (Na0.5K0.5)0.945Li0.055Nb1-xSbxO3 Solid Solutions", J. Am. Ceram. Soc., 90, 3070 (2007).

S. Zhang, R. Xia, T. R. Shrout, J. Zang, and J. Wang, "Piezoelectric Properties in Perovskite 0.948(K0.5Na0.5) NbO3-0.052LiSbO3 lead-free ceramics", J. App. Phys., 100, 104108 (2006).

Lee, C. et al., "Sol-gel derived PZT force sensor for scanning force microscopy", Mater. Chem. Phys., 44: 25-29 (1996).

Lee, C. et al., "Self-excited piezoelectric PZT microcantilevers for dynamic SFM—with inherent sensing and actuating capabilities", Sensors and Actuators, A72: 179-188 (1999).

Lee, J. H. et al., "Label free novel electrical detection using micromachined PZT monolithic thin film cantilever for the detection of C-reactive protein", Biosensors and Bioelectronics, 20: 269-275 (2004).

Lee, J. H. et al., "Effect of mass and stress on resonant frequency shift of functionalized Pb(Zr0.52Ti0.48)O3 thin film microcantilever for the detection of C-reactive protein", Appl. Phys. Lett., 84(16): 3187-3189 (2004).

Lee, J. H. et al., "Immunnoassay of prostate-specific antigen (PSA) using resonant frequency shift of piezoelectric nanomechanical microcantilever", Biosensors and Bioelectronics, 20: 2157-2162 (2005).

Lee, S. S. et al., "Self-Excited Piezoelectric Cantilever Oscillators", The 8th International Conference on Solid-State Sensors and Actuators, and Eurosensors IX, Stockholm, Sweden: 417-420 (1995).

Lee, Y. et al., "A Piezoelectric Micro-Cantilever Bio-Sensor Using the Mass-Microbalancing Technique With Self-Excitation", The 13th International Conference on Solid-State Sensors, Actuators, and Microsystems, Seoul, Korea: 644-647 (2005).

Li, S. et al., "The intrinsic nature of nonlinear behavior observed in lead zirconate titanate ferroelectric ceramic", J. Appl. Phys., 69(10): 7219-7224 (1991).

Li, X. et al., "Detection of water-ice transition using a lead zirconate titanate/brass transducer", J. Appl. Phys., 92(1): 106-111 (2002).

Lin, Z. et al., "Operation of an Ultrasensitive 30-MHz Quartz Crystal Microbalance in Liquids", Anal. Chem., 65(11): 1546-1551 (1993).

Liu, W. et al., "Preparation and orientation control of Pb1.1(Zr0.3Ti0.7)O3 thin films by a modified sol-gel process", Mat. Lett., 46: 239-243 (2000).

Luo, H. et al., "Synthesis of PMN and 65PMN-35PT Ceramics and Films by a New Suspension Method", Perovskite, Piezoelectric, and Dielectric Ceramics: 251-260.

Luo, H. et al., "Comparison in the Coating of Mg(OH)2 on Micron-Sized and Nanometer-Sized Nb2O5 Particles", Int. J. Appl. Ceram. Technol., 1(2): 146-154 (2004).

Luo, H., "Colloidal Processing of PMN-PT Thick Films for Piezoelectric Sensor Applications", A Thesis Submitted to the Faculty of Drexel University in Jun. 2005.

Maki, K. et al., "Evaluation of Pb(Kr,Ti)O3 Films Derived from Propylene-Glycol-Based Sol-Gel Solutions", Jpn. J. Appl. Phys., 39(9B): 5421-5425 (2000).

Maraldo, D. et al., "Resonant-mode millimeter sized cantilever biosensor for continuous detection of proteins and pathogens in flowing liquids," Dept. Of Chem. And Biological Eng., 1-21.

Matsui, Y. et al., "Highly Oxidation-Resistant TiN Barrier Layers for Ferroelectric Capacitors", Jpn. J. Appl. Phys., 36 (3B): 1586-1588 (1997).

Mazza, E. et al., Biomechanics, http://www.zfm.ethz.ch/e/res/bio/, 1-10.

McGovern, J.P. et al., "Real-Time *Salmonella* Detection Using Lead Zirconate Titanate-Titanium Microcantilevers", Mater. Res. Soc. Symp. Proc., 845: AA3.8.1-AA3.8.6 (2005).

Mueller, V. et al., "Nonlinearity and scaling behavior in donor-doped lead zirconate titanate piezoceramic", Appl. Phys. Lett., 72(21): 2692-2694 (1998).

Mulvihill, M. L. et al., "The Role of Processing Variables in the Flux Growth of Lead Zinc Niobate-Lead Titanate Relaxor Ferroelectric Single Crystals", Jpn. J. Appl. Phys., 35(7): 3984-3990 (1996).

Niedziolka, J. et al., "Charaterisation of gold electrodes modified with methyltrimethoxysilane and (3-mercaptopropyl)trimethoxysilane sol-gel processed films", J. Electroanalytical Chem., 578: 239-245 (2005).

Nguyen, L. T. T. et al., "Synthesis and characterization of a photosensitive polyimide precursor and its photocuring behavior for lithography applications", Optical Materials, 29: 610-618 (2007).

Oden, P. I. et al., "Viscous drag measurements utilizing microfabricated cantilevers", Appl. Phys. Lett., 68(26): 3814-3816 (1996).

Ohnmacht, M. et al., "Microcoils and microrelays—an optimized multilayer fabrication process", Sensors and Actuators, 83: 124-129 (2000).

Park, G.T. et al., "Measurement of piezoelectric coefficients of lead zirconate titanate thin films by strain-monitoring pneumatic loading method", Appl. Phys. Lett., 80(24): 4606-4608 (2002).

Park, S.E. et al., "Ultrahigh strain and piezoelectric behavior in relaxor based ferroelectric single crystals", J. Appl. Phys., 82(4): 1804-1811 (1997).

Piezo Systems, Inc., "Piezoceramine Sheets and Their Properties", Piezo Systems, Inc. Catalog: 1-3 (2007).

Pons, T. et al., "Solution-phase single quantum dot fluorescence resonance energy transfer", J. Amer. Chem. Soc., 128(47): 15324-15331 (2006). Abstract Only.

Ren, W. et al., "Non linear strain and DC bias induced piezoelectric behaviour of electrostrictive lead magnesium niobate-lead titanate ceramics under high electric fields", J. Phys. D: Appl. Phys., 35: 1550-1554 (2002).

Ren, W. et al., "Nonlinear behavior of piezoelectric lead zinc niobate-lead titanate single crystals under ac electric fields and dc bias", Appl. Phys. Lett., 83(25): 5268-5270 (2003).

Rosenberg, RD et al., "Effects of age, breast density, ethnicity and estrogen replacement therapy on screening mammographic sensitivity and cancer stage at diagnosis: review of 183,134 screening mammograms in Albuquerque, New Mexico", Radiology, 209(2): 511-5118 (1998). Abstract Only.

Saito, Y. et al., "Lead-free piezoceramics", Nature, 432: 84-87 (2004).

Schemmel, A. et al., "Single molecule force spectrometer with magnetic force control and inductive detection", Rev. Sci. Instrum., 70(2): 1313-1317 (1999).

Shen, Z. et al., "Microfabrication of Miniaturized PZT/SiO2 Piezoelectric Microcantilever for Rapid, Direct, In-situ Biosensing", MRS Fall Meeting, Boston: 1-23 (2005).

Shen, Z. et al., "Self-exciting, self-sensing PbZr0.53Ti0.47O3/SiO2 piezoelectric microcantilevers with femtogram/Hertz sensitivity", Appl. Phys. Lett., 89: 023506-1-023506-3 (2006).

Shih, W. et al., "Simultaneous liquid viscosity and density determination with piezoelectric unimorph cantilevers", J. Appl. Phys., 89(2): 1497-1505 (2001).

Shih, W. et al., "Ultrasensitive Pathogen Quantification in Drinking Water Using Highly Piezoelectric Microcantilevers", Amer. Chem. Soc., Chapter 23, 179-185 (2005).

Shih, W. et al., "Nanosensors for Environmental Applications", Nanotechnologies for the Life Sciences, 5: 271-293 (2005).

Straub, V. et al., "Contrast Agent-Enhanced Magnetic Resonance Imaging of Skeletal Muscle Damage in Animal Models of Muscular Dystrophy", Magn. Reson. Med., 44: 655-659 (2000).

Thompson, W. R. et al., "Hydrolysis and Condensation of Self-Assembled Monolayers of (3-Mercaptopropyl) trimethoxysilane on Ag and Au Surfaces", Langmuir, 13: 2291-2302 (1997).

Thundat, T. et al., "Detection of mercury vapor using resonating microcantilevers", Appl. Phys. Lett., 66(13): 1695-1697 (1995).

Tslonsky, M. et al., "Sol-Gel-Derived Ceramic-Carbon Composite Electrodes: Introduction and Scope of Applications", Anal. Chem., 66: 1747-1753 (1994).

Tu, Y. L. et al., "A study of the effects of process variables on the properties of PZT films produced by a single-layer sol-gel technique", J. Mater. Sci., 30: 2507-2516 (1995).

Udayakumar, K. R. et al., "Thickness-dependent electrical characteristics of lead zirconate titanate thin films", J. Appl. Phys., 77(8): 3981-3986 (1995).

Wang, Q.M. et al., "Nonlinear piezoelectric behavior of ceramic bending mode actuators under strong electric fields", J. Appl. Phys., 86(6): 3352-3360 (1999).

Wang, Y. et al., "Tactile Mapping of Palpable Abnormalities for Breast Cancer Diagnosis".

Ward, M. D. et al., "In Situ Interfacial Mass Detection with Piezoelectric Transducers", Science, 249: 1000-1007 (1990).

Wellman, P. S. et al., "Breast Tissue Stiffness in Compression is Correlated to Histological Diagnosis", http://biorobotics.harvard.edu/pubs/mechprops: 1-15.

Wellman, P. S. et al., "Tactile Imaging of Breast Masses", Arch. Surg., 136: 204-208 (2001).

Amanuma, K. et al., "Crystallization behavior of sol-gel derived Pb(Zr,Ti)O3 thin films and the polarization switching effect on film microstructure", Appl. Phys. Lett., 65(24): 3140-3142 (1994).

Ammari, H. et al., "T-Scan Electrical Impedance Imaging System for Anomaly Detection", Siam J. Appl. Math., 65(1): 252-266 (2004).

Baselt, D. R. et al., "Biosensor based on force microscope technology", J. Vac. Sci. Technol. B, 14(2): 789-793 (1996).

Birnie, III, D. P. et al., "Coating uniformity and device applicability of spin coated sol-gel PXT films", Microelectronic Engineering, 29: 189-192 (1995).

Bondoux, C. et al., "MgO insulating films prepared by sol-gel route for SiC substrate", J. Europe. Ceramic Soc., 25: 2795-2798 (2005).

Brito, R. et al., "Adsorption of 3-mercaptopropyltrimethoxysilane and 3-aminopropyltrimethoxysilane at platinum electrodes", J. Electroanalytical Chem., 520: 47-52 (2002).

Campbell, G.A., et al., "Piezoelectric excited millimeter-sized cantilever (PEMC) sensor detects *Escherichia coli* O157:H7 in two-hour incubated samples at 4 CFU per gram of beef," J. of Rapid Methods and Automation in Mirobiology, 1-39.

Campbell, G.A., et al., "Detection and quantification of proteins using self-excited PZT-glass millimeter-sized cantilever," Biosensors and Bioelectronics, 26-36.

Campbell, G.A., "Piezoelectric-excited millimeter-sized cantilever (PEMC) sensors detect *Bacillus anthracis* at 300 spores/mL," Biosensors and Bioelectronics, 37-45.

Campbell, G.A., et al., "kinetics of *Bacillus anthracis* spore binding to antibody functionalized PEMC sensors in presence of *Bacillus thuringiensis* and *Bacillus cereus*," J. Publications, Am. Chem. Soc. 25 pages.

Campbell, G.A., et al., "*Escherichia coli* O157:H7 detection limit of millimeter-sized PZT cantilever sensors in 700 cells/mL," Analytical Sci., 11-13.

Campbell, G.A., et al., "Detection of pathogen *Escherichia coli* O157:H7 using self-excited PZT-glass microcantilevers," Biosensors and Boelectronics, 14-25.

Campbell, G.A., "Detection of *Staphylococcus enterotoxin* B at pictogram levels using piezoelectric-excited millimeter-sized cantilever sensors," Submitted on line to J. of Analytical Chem., 1-24.

Campbell, G.A., et al., "Detect *Escherichia coli* 0157:H7 in ground beef samples using piezoelectric excited millimeter sized cantilever (PEMC) sensors," Submitted on-line to Biosensors and Bioelectronics, 2-34.

Campbell, G.A., et al., "A method for measuring *Escherichia coli* O157:H7 at 1 cell/mL in 1 liter sample using antibody functional piezoelectric-excited millimeter sized cantilever sensor," Paper submitted on-line to J. of Analytical Chemistry. 1-23.

Capobianco, J. A., et al., "Methyltrimethoxysilane-insulated piezoelectric microcantilevers for direct, all-electrical biodetection in buffered aqueous solutions", Rev. Sci. Instrum., 77: 125105-1-125105-6 (2006).

Capobianco, J. A., et al., "3-mercaptopropyltrimethoxysilane as insulating coating and surface for protein immobilization for piezoelectric microcantilever sensors", Rev. Sci. Instrum., 78: 046106-1-046106-3 (2007).

Carlier, S. G., et al., "Elastography", J. Cardiovasc Risk, 9(5): 237-245 (2002).

Carr, D.W., et al., "Fabrication of nanoelectromechanical systems in single crystal silicon using silicon on insulator substrates and electron beam lithography," J. Vac. Sci. Technology, B, 5(6), 2760-2763.

Che, G. et al., "Molecular recognition based on (3-mercaptopropyl) trimethoxysilane modified gold electrodes", J. Electroanalytical Chem., 417: 155-161 (1996).

Chen, G.Y. et al., "Adsorption-induced surface stress and its effects on resonance frequency of microcantilevers", J. Appl. Phys., 77(8): 3618-3622 (1995).

Chen, X. et al., "Electrochemical and Spectroscopic Characterization of Surface Sol-Gel Processes", Langmuir, 20 (20): 8762-8767 (2004).

Cho, S. H. et al., "Micro-scale metallization on flexible polyimide substrate by Cu electroplating using SU-8 photoresist mask", Thin Solid Films, 475: 68-71 (2005).

Duval, F.F.C. et al., "Stable TiO2/Pt electrode structure for lead containing ferroelectric thick films on silicon MEMS structures", Thin Solid Films, 444: 235-240 (2003).

Feili, D. et al., "Encapsulation of organic field effect transistors for flexible biomedical microimplants", Sensors and Actuators, A120: 101-109 (2005).

Ferrini, R. et al., "Screening Mammography for Breast Cancer: American College of Preventive Medicine Practice Policy Statement", www.acpm.org/breast, pp. 1-4 (2005).

Fritz, J. et al., "Translating Biomolecular Recognition into Nanomechanics", Science, 288: 316-318 (2000).

Fung, Y. S. et al., "Self-Assembled Monolayers as the Coating in a Quartz Piezoelectric Crystal Immunosensor to Detect *Salmonella* in Aqueous Solution", Anal. Chem., 73: 5302-5309 (2001).

Gao, L. et al., "Imaging of the elastic properties of tissue: A review", Ultrasound in Med. & Biol., 22(8): 959-977 (1996). Abstract Only.

Greenleaf, J. F. et al., "Selected Methods for Imaging Elastic Properties of Biological Tissues", Annu. Rev. Biomed. Eng., 5: 57-78 (2003).

Gu, H. et al., "Single-Calcination Synthesis of Pyrochlore-Free 0.9Pb(Mg1/3Nb2/3)O3-0.1PbTiO3 and Pb (Mg1/3Nb2/3)O3 Ceramics Using a Coating Method", J. Am. Ceram. Soc., 86(2): 217-221 (2003).

Haccart, T. et al., "Evaluation of niobium effects on the longitudinal piezoelectric coeffecients of Pb(Zr,Ti)O3 thin films", Appl. Phys. Lett., 76(22): 3292-3294 (2000).

Han, W. et al., "A magnetically driven oscillating probe microscope for operations in liquids", Appl. Phys. Lett., 69(26): 4111-4113 (1996).

Hiboux, S. et al., "Mixed titania-lead oxide seed layers for PZT growth on Pt(111): a study on nucleation, texture and properties", J. Europe. Ceram. Soc., 24: 1593-1596 (2004).

Hwang, I.H. et al., "Self-actuating biosensor using a piezoelectric cantilever and its optimization", Journal of Physics: Conference Series 34, pp. 362-367, 2006.

Hwang, K.S. et al., "In-situ quantitative analysis of a prostate-specific antigen (PSA) using a nanomechanical PZT cantilever", Lab Chip, 4: 547-552 (2004).

Ilic, B. et al., "Mechanical resonant immunospecific biological detector", Appl. Phys. Lett., 77(3): 450-452 (2000).

Itoh, T. et al., "Self-excited force-sensing microcantilevers with piezoelectric thin films for dynamic scanning force microscopy", Sensor and Actuators, A54:477-481 (1996).

Jung, S.K. et al., "Polymeric Mercaptosilane-Modified Platinum Electrodes for Elimination of Interferants in Glucose Biosensors", Anal. Chem., 68: 591-596 (1996).

Kanda, T. et al., "A flat type touch probe sensor using PZT thin film vibrator", Sensors and Actuators, 83: 67-75 (2000).

Katiyar, P. et al. "Electrical properties of amorphous aluminum oxide thin films", Acta Materialia, 53: 2617-2622 (2005).

Keller, A. et al., "Reliability of Computed Tomography Measurements of Paraspinal Muscle Cross-Sectional Area and Density in Patients With Chronic Low Back Pain", Spine, 28(13): 1455-1460 (2003).

Kelly, J. et al., "Effect of Composition on the Electromechanical Properties of (1-x)Pb(Mg1/3Nb2/3)O3-xPbTiO3 Ceramics" J. Am. Ceram. Soc., 80(4): 957-964 (1997).

Khabari, A. et al., "Partially ionized beam deposition of parylene". J. Non-Crystalline Solids, 351: 3536-3541 (2005).

Kim, S.H. et al., "Influence of Al2O3 diffusion barrier and PbTiO3 seed layer on microstructural and ferroelectric charachteristics of PZT thin films by sol-gel spin coating method," Thin Solid Films, 305: 321-326 (1997).

Kim, S.J. et al., "Fabrication and Characterization of Pb(Zr,Ti)O3 Microcantilever for Resonance Sensors," Jpn. J. Appl. Phys., 42(3): 1475-1478 (2003).

Klissurska, R.D. et al. "Microstructure of PZT sol-gel films on Pt substrates with different adhesion layers," Microelectronic Engineering, 29: 297-300 (1995).

Kruse, S.A. et al., "Tissue characterization using magnetic resonance elastography: preliminary results," Phys. Med. Biol., 45: 1579-1590 (2000).

Kumar, V. et al., "A Simple System for the Preparation of Submicrometer Lead Titanate Powders by the Sol-Gel Method," J. Am. Ceram. Soc., 79(10): 2775-2778 (1996).

Kwok, CLK. et al., "Low temperature perovskite formation of lead zirconate titanate thin films by a seeding process," J. Mater. Res., 8(2): 339-344 (1993).

Wellman, P. S. et al., "Tactile Imaging: A Method for Documenting Breast Lumps".

Weng, L. et al., "Effect of acetylacetone on the preparation of PZT materials in sol/gel processing", Mater. Sci. Engin., B96: 307-312 (2002).

Wilson, L S et al., "Elastography—the movement begins", Phys. Med. Biol., 45: 1409-1421 (2000).

Wilson, L., et al., "Pezoelectric-excited millimeter-sized cantilever (PEMC) sensor provides viscosity and density measurements," Submitted to Review of Scientific Instruments, 1-26.

Yi, J. W. et al., "Effect of length, width, and mode on the mass detection sensitivity of piezoelectric unimorph cantilevers", J. Appl. Phys., 91(3): 1680-1686 (2002).

Yi, J. W. et al., "In situ cell detection using piezoelectric lead zirconate titanate-stainless steel cantilevers", J. Appl. Phys., 93(1): 619-625 (2003).

Zhao, Q. et al., "Array adsorbent-coated lead zirconate titanate (PZT)/stainless steel cantilevers for dimethyl methylphosphonate (DMMP) detection", Sensors and Actuators, B117(1): 74-79 (2006). Abstract Only.

Zhou, J. et al., "Zeolite-modified microcantilever gas sensor for indoor air quality control," Sensors and Actuators B, Oct. 1, 2003, 94(3), 337-342.

Zhu, D.M. et al., "Thermal conductivity and electromechanical property of single-crystal lead magnesium niobate titanate", Appl. Phys. Lett., 75(24): 3868-3870 (1999).

Data of Commercially Available Product, EDO Corporation: 1-8 (1999).

Data of Commercially Available Product, APC International, Ltd.: 1-2 (2005).

Campbell, G.A., et al., "Use of Piezoelectric-Excited millimeter Sized Cantilever Sensors to Measure Albumin Interaction with Self-Assembled Monolayers of Alkanethiols Having Different Functional Headgroups," Anal. Chem. 78, 2328-2334 (2006).

Campbell, G.A., et al., "Method of measuring Bacillus anthracis spores in the Presence of copious amounts of Bacillus thurigiensis and Bacillus cereus," Anal. Chem. 79, 1145-1152 (2007).
Campbell, G.A., et al., "PEMC sensor's mass change sensitivity is 20 pg/Hz under liquid immersion," Biosensors and Bioelectronics, 22, 35-41 (2006).
Campbell, G.A., et al., "Detection of *Bacillus anthracis* spores and a model protein usings PEMC sensors in a flow cell at 1 mL/min," Biosensors and Bioelectronics, 22, 78-85 (2006).
Campbell, G.A., et al., "Detection of airborne *Bacillus anthracis* spores by an integrated system of an air sampler and a cantilever immunosensor," Sensors and Actuators B 127, 376-382 (2007).
Maraldo, et al., "Method for Label-Free Detection of Femtogram Quantities of Biologics in Flowing Liquid Samples," Anal. Chem. 79, 2762-2770 (2007).
Maraldo, et al., "Detection and confirmation of staphylococcal enterotoxin B in apple juice and milk using piezoelectric-excited millimeter-sized cantilever sensors at 2.5 fg/mL," Anal Chem. 79, 7636-7643 (2007).
Maraldo, et al., "Method for Quantification of a Prostate Cancer Biomarker in Urine without Sample Preparation," Anal. Chem. 79, 7683-7690 (2007).
Maraldo, et al., "10-Minute assay for detecting *Escherichia coli* O157:H7 in ground beef samples using piezoelectric-excited millimeter-size cantilever sensors." Journal of Food Protection, vol. 70, No. 7, 1670-1677 (2007).
Maraldo, et al., "Preapration-Free Method for Detecting *Escherichia coli* O157:H7 in the Presence of Spinach, Spring Lettuce Mix, and Ground Beef Particulates," Journal of Food Protection, vol. 70, No. 11, 2651-2655 (2007).
Rijal, et al., "PEMC-based method of measuring DNA hybridization at femtomolar concentration directly in human serum and in the presence of copious noncomplementary strands," Anal. Chem., 79, 7392-7400 (2007).

* cited by examiner

SPECIFICITY AND SENSITIVITY ENHANCEMENT IN CANTILEVER SENSING

RELATED APPLICATION DATA

This application is a continuation-in-part of U.S. patent application Ser. No. 11/943,790, filed on Nov. 21, 2007, currently pending, under 35 U.S.C. §120, which, in turn, is a non-provisional of U.S. provisional application No. 60/867,245, filed on Nov. 27, 2006, pursuant to 35 U.S.C. §119(e), a non-provisional of U.S. provisional patent application No. 61/046,899, filed on, Apr. 22, 2008, pursuant to 35 U.S.C. §119(e), and a non-provisional of U.S. provisional patent application No. 60/977,776, filed on Oct. 5, 2007, pursuant to 35 U.S.C. §119(e)

STATEMENT OF GOVERNMENT INTEREST

This invention was reduced to practice with Government support under Grant No. R01 EB000720 awarded by the National Institutes of Health; the Government is therefore entitled to certain rights to this invention.

BACKGROUND OF THE INVENTION

1. Field of the Invention

The invention is directed to a sensor system and a method for providing a higher degree of specificity and sensitivity in cantilever sensing. More specifically, the invention relates to the binding of substrates to target specific receptors to improve detection specificity and sensitivity in cantilever sensors.

2. Description of the Related Technology

The National Center for Health Statistics reports that cancer is the second leading cause of death in the United States, accounting for 22.7% of deaths in 2003. Many of these deaths may have been prevented by early detection and diagnosis, which offers the most chance of successfully fighting cancer. In an attempt to advance early detection technologies, scientists have been trying to develop biosensors capable of identifying minute amounts of specific proteins in a sample that contains multiple protein species to create a sensitive blood test for detecting cancer markers. The presence of minute amounts of cancer marker proteins or debris shed by cancer cells present in patients' blood, however, is typically overshadowed by the large amount of proteins normally contained in serum samples. The lack of sufficient detection specificity and sensitivity, therefore, is a critical and currently unresolved issue hindering the development of viable diagnostic tools based on protein detection.

One of the most common commercially available sensor systems for biosensing applications, the quartz crystal microbalance (QCM), uses thickness-mode resonance detection. The detection sensitivity of a QCM is related to the resonance frequency and the thickness of the quartz membrane. A resonance frequency of about 5 MHz, corresponding to a quartz membrane thickness of 330 μm, enables a minimum detectable mass density of about $10^{-9}$ g/cm². Sensitivity is therefore generally limited to a range of about $10^{-8}$ g/Hz. Although convenient and economical, the QCM has a relatively low detection sensitivity in the ng/ml range. By contrast, protein detection for diagnostic purposes generally requires a sensitivity in the range of pg/ml to fg/ml.

Another popular sensor system, ELISA, for example, has a detection sensitivity of 0.01-50 ng/ml for proteins in solution, depending on the affinity of antibodies. Detection using the ELISA system, however, is time intensive and requires labeling. Recently, H. Zhang, et al., "A Sensitive and High-Throughput Assay to Detect Low-Abundance Proteins in Serum," *Nature Medicine* 12 (4) 473-477 (2006) showed that ELISA detection can be enhanced $10^5$ fold (5 pg/ml) by replacing enzymes with RNA polymerase in HER-2 detection. Even with this improvement, processing speed and expense remain a significant concern.

Some methods for increasing the sensitivity of current sensors are known. One example of this is found in J.-W. Park, S. Kurosawa, H. Aizawa Y. Goda, M. Takai and K. Ishihara, "Piezoelectric Immunosensor for Bisphenol A Based on Signal Enhancing Step With 2-methacrolyloxyethyl Phosphorylcholine Polymeric Nanoparticle," *Analyst*, 131, 155-162 (2006).

Current state of the art sensors, therefore, are incapable of both real-time label free detection and highly sensitive detection. This shortcoming is particularly problematic for applications involving biological samples, which typically have a high protein concentration that creates noise, interfering with detection sensitivity. For example, the ability to detect minute amounts of a target protein or DNA in sera is hindered by the background serum protein concentrations in the test sample. The large amount of protein in sera significantly dilutes biomarker concentration, which in turn reduces detection sensitivity.

Current sensors also lack an independent means for verifying detection results. An independent verification means would efficiently minimize false-positive and false-negative results, which is particular critical to the field of medical diagnostics and cancer detection. Therefore, there exists a need to develop a sensor system that enables highly sensitive label free real time detection as well as verification of the detection results.

SUMMARY OF THE INVENTION

The present invention is directed to a sensor system and a method for its use. The system uses substrates provided with target specific receptors to enhance detection sensitivity.

In a first aspect, the invention relates to a sensor system including at least one sensor including a plurality of target specific receptors capable of binding a specific target molecule or compound. A detector is operatively associated with said sensor and is capable of detecting a change in at least one property of said sensor. Substrates are positioned to contact said at least one sensor, each said substrate having at least one target specific receptor directly or indirectly bound to said substrate, said target specific receptor being capable of binding the target molecule or compound. The target specific receptors bound to said substrates do not bind to the same binding site on said target molecule or compound as said target specific receptors of said sensor.

Another aspect of the invention involves a method for using the sensor system comprising exposing a sensor system to a test sample and determining a presence or concentration of a target molecule or compound.

DETAILED DESCRIPTION OF THE PREFERRED EMBODIMENTS

For illustrative purposes, the principles of the present invention are described by referencing various exemplary embodiments thereof. Although certain embodiments of the invention are specifically described herein, one of ordinary skill in the art will readily recognize that the same principles are equally applicable to, and can be employed in other compositions and methods. Before explaining the disclosed embodiments of the present invention in detail, it is to be understood that the invention is not limited in its application to the details of any particular embodiment shown. The terminology used herein is for the purpose of description and not of limitation. Further, although certain methods are described with reference to certain steps that are presented herein in certain order, in many instances, these steps may be performed in any order as may be appreciated by one skilled in the art, and the methods are not limited to the particular arrangement of steps disclosed herein.

The invention is directed to a sensor system 1 and method for enhanced detection using a substrate bound to a target specific receptor. The system enables rapid real time label free highly specific and sensitive detection and, optionally, may further enable a means for rapid independent verification of the detection results. The sensor system 1 may be used for the detection of any molecule or compound in any sample medium for which a receptor and target pair is available.

Figure 1A:
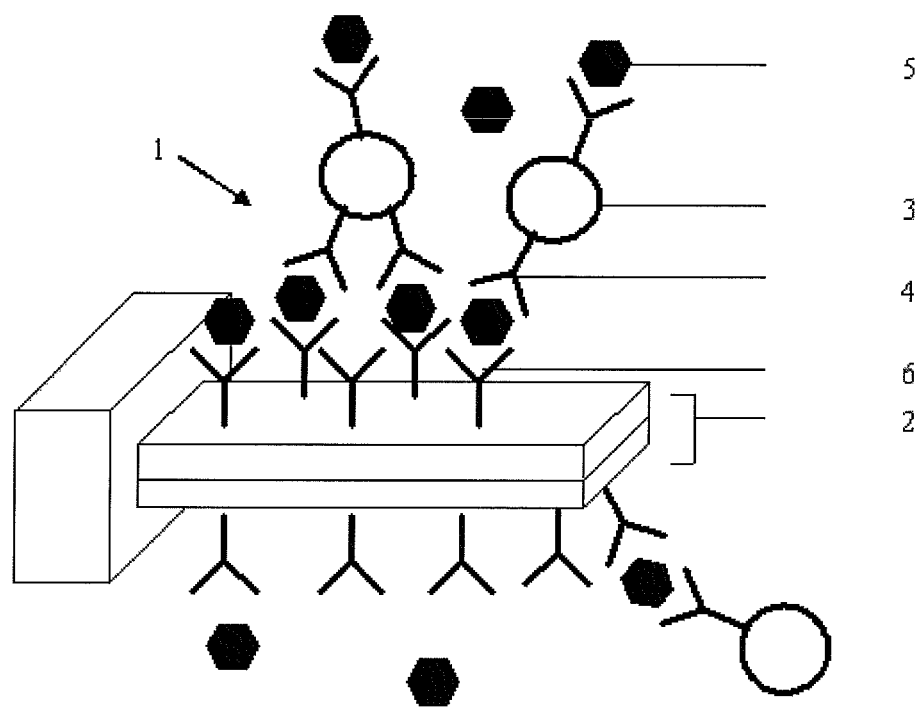
FIG. 1(a) is a schematic representation of compound detection using the sensor system in accordance with one embodiment of the present invention.

As shown in FIG. 1, the sensor system 1 includes at least one sensor 2 provided with receptors attached to at least a surface of sensor 2. Receptors 6 are preferably selected for their ability to bind to a particular target molecule or compound or a class of target molecules or compounds. Receptors 6 may be bound to the surface of sensor 2 in any suitable conventional manner. As a result, sensor 2 may be rendered capable of detecting the presence of a target molecule or compound 5 since target 5 will bind to receptors 6 on the surface of sensor 2. In one embodiment, the resultant shift in the mechanical resonance frequency of the sensor 2 due to the binding of target 5 may be monitored to indicate the presence of target 5 in the media to which the sensor 2 and receptors 6 have been exposed.

Sensor 2 may have any suitable structural configuration and may be constructed from any suitable material that enables detection. Sensor 2 may be configured as a cantilever sensor in which binding stresses due to the bound target 5 can be detected. Detection can be facilitated, for example, by the provision of a piezoelectric material in association with sensor 2 whereby the resonance frequency of sensor 2 can be measured by measuring the output from the piezoelectric material and relating that resonance frequency shift to the binding of target 5 and the associated binding stress exerted on sensor 2. One particularly useful embodiment of sensor 2 is in the form of a piezoelectric microcantilever since this embodiment facilitates sensitivity at very low concentrations of target 5. Exemplary piezoelectric microcantilevers may have detection sensitivities in the range of about fg/ml to about pg/ml, depending on the specific sensing application.

Figures 2A, 2B:
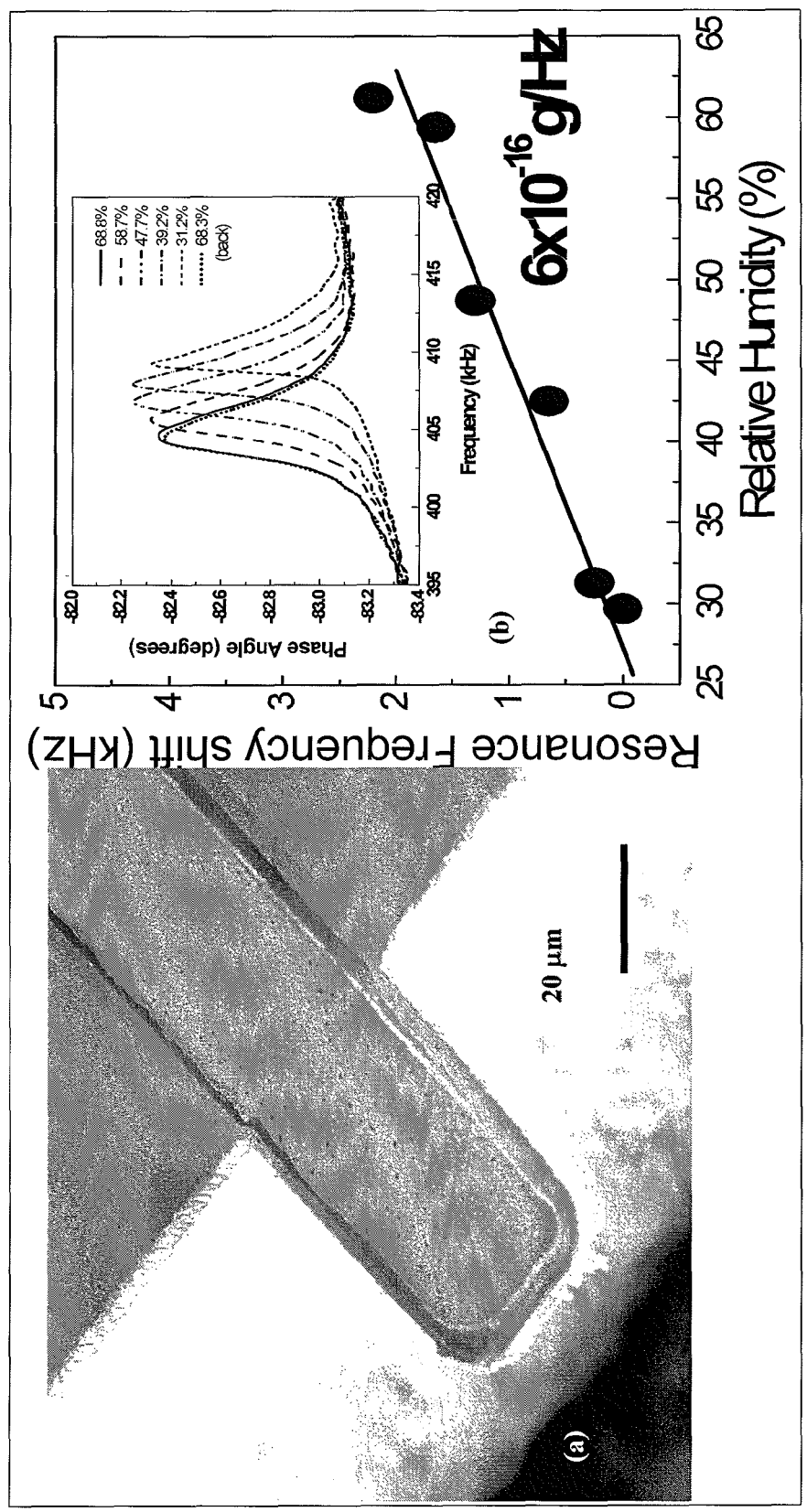
FIG. 2(a) is a scanning electron micrograph of a 40 μm long PZT/SiO$_2$ piezoelectric microcantilever sensor.
FIG. 2(b) is a graph of the resonance frequency shift versus relative humidity of the sensor of FIG. 2(a). The insert of FIG. 2(b) shows the resonance spectra at various levels of relative humidity.

FIGS. 2(a) and 2(b) show one preferred embodiment wherein the sensor 2 is a piezoelectric microcantilever that can detect proteins in solution. Sensor 2 of FIGS. 2(a)-2(b) has been demonstrated to have a sensitivity of at least $10^{-16}$ g/Hz Z. Shen, W. Y. Shih, and W.-H. Shih, "Self-Exciting, Self-Sensing PZT/SiO$_2$ Piezoelectric Microcantilever Sensors with Femtogram/Hz Sensitivity," *Appl. Phys. Lett* 89, 023506 (2006).

Figure 1B:
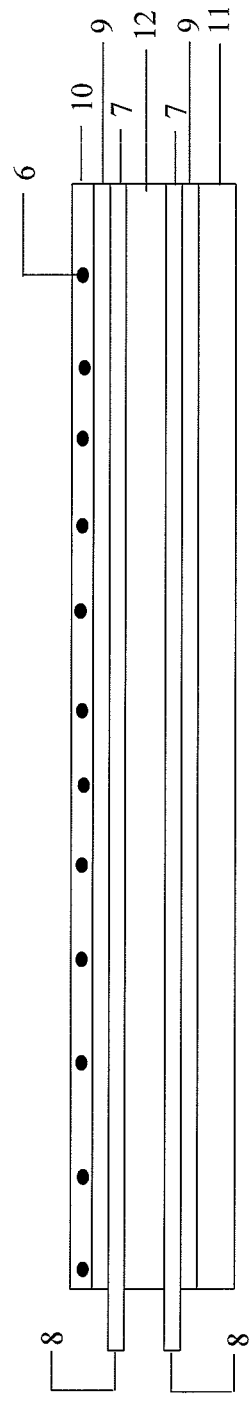
FIG. 1(b) is a cross-sectional view of a first embodiment of a sensor in accordance with the present invention.
Figure 1C:
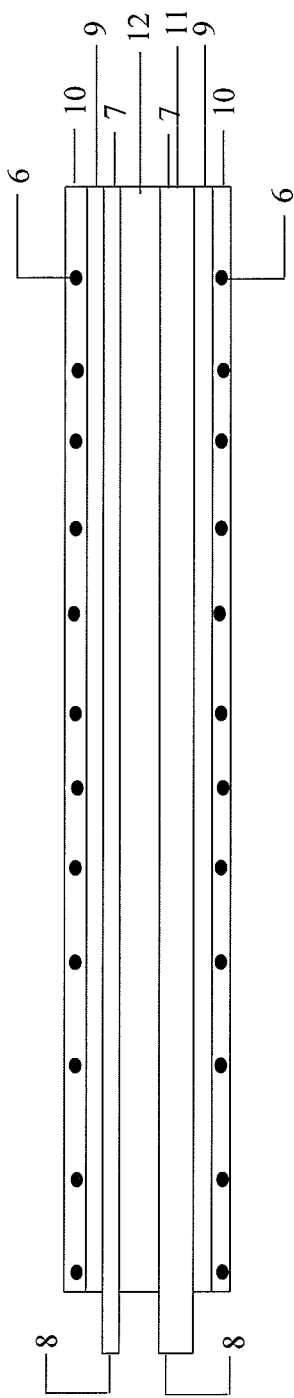
FIG. 1(c) is a cross-sectional view of a second embodiment of a sensor in accordance with the present invention.

FIG. 1(b) is another preferred embodiment wherein the sensor is a piezoelectric microcantilever comprising conductive elements 7 operatively associated with electrical leads 8, an electrically insulating layer 9, a receptor immobilization layer 10, target specific receptors 6, at least one non-piezoelectric layer 11 and at least one piezoelectric layer 12. In one embodiment, as shown in FIG. 1(c), the non-piezoelectric layer 11 may also function as a conductive layer 7, wherein an insulation layer 9 and an immobilization layer 10 may also be present on the surface of the non-piezoelectric layer. The piezoelectric microcantilever sensor detects the presence of a target molecule or compound by monitoring a shift in the mechanical resonance frequency of the sensor due to a change in mass or elastic modulus of the cantilever portion when target molecules or compounds bind to receptors 6. Target specific receptor antibodies 6, for example, may be immobilized on at least a surface of the piezoelectric microcantilever sensor enabling binding of a target protein 5. This binding causes the resonance frequency of the piezoelectric microcantilever to shift and generates a real-time label-free detection signal which corresponds to the amount of a target proteins 5 bound to the sensor, thus allowing determination of the concentration of a target protein 5.

The sensor system 1 of the present invention provides binding substrates 3 in a sample material which is to be sensed. Each binding substrate 3 may be provided with target specific receptors 4 bound to binding substrate 3. Target specific receptors 4 include binding sites which are specific for binding target molecules or compounds 5. Thus, in the embodiment of the invention shown in FIG. 1, substrates 3 are provided with at least one, preferably target specific receptors 4 bound to each substrate 3. In this embodiment, each target specific receptor 4 includes one binding site which is specific for binding target molecule or compound 5. In one embodiment, target specific receptors 4 are employed to indirectly bind substrate 3 to sensor 2 via binding of target specific receptors 4 to target molecules or compounds 5 that are also bound to target specific receptors 6 bound to a surface of sensor 2, as shown in FIG. 1. In embodiments where it is desirable to determine the concentration of the target 5, in addition to being able to detect the presence of target 5, it is beneficial to select substrates 3 such that the average number of target specific receptors 4 on each substrate 3 is known. It is also advantageous to select target specific receptors 4 and 6 such that the average number of binding sites on each target specific receptor 4, 6 is known. In this manner, the resonance frequency shift can be mathematically related to the concentration of target 5 in the sample by calibration of the sensor system.

In an embodiment of the invention where it is desirable to measure the concentration of target molecules or compounds 5, a key aspect of target specific receptors 4 is their ability to selectively bind a specific target molecule or compound 5 at a different binding site on target 5 than is used to form the bond between target 5 and target specific receptors 6. Thus, target specific receptors 4 do not compete with target specific receptors 6 immobilized on a surface of sensor 2 for binding sites on target molecules or compounds 5. In one embodiment, each substrate 3 includes one target specific receptor 4, in which case target specific receptors 4 function to bind substrates 3 to targets 5 which targets 5 will also be bound to target specific receptors 6 on the surface of sensor 2. In this manner, the weight of target specific receptors 4 and substrate 3 is added to the weight of the bound target molecules or compounds 5 thereby enhancing the detection sensitivity of sensor 2. Detection sensitivity is enhanced since lower concentrations of target 5 can be employed to generate a larger signal from sensor 2 due to the added binding stress providing by the additional binding of target specific receptors 4 and substrates 3 to the surface of sensor 2. Without wishing to be bound by theory, selecting for micron sized or larger substrates 3, the large mass of the bound substrates and stress generated by the bound substrates will dramatically enhance the detection signal even when there are only few target molecules on the sensor surface. The micron-size target specific receptors 4 bound to substrate 3 are estimated to be able to enhance detection sensitivity by a factor of approximately $10^6$.

The target specific receptors 4 may be any receptor such as specially synthesized cavitants, DNA oligonucleotides, proteins, single chain variable fragments (scFvs), enzymes, antibodies, etc. which selectively bind a particular cell, protein, antigen, pathogen, etc. For example, when trying to detect tumors, monomeric and dimeric anti-tumor scFv molecules, composed of variable light and heavy chains of antibody molecule anti-ECD scFV, which react to cancer markers are useful target specific receptors. Similarly, when trying to detect *Bacillus anthracis* ("BA"), antibodies specific to BA spore surface antigens may be used.

In one embodiment, the target specific receptors 4 are high affinity, high specificity non-competing secondary antibodies which target a specific antigen; a primary antibody located on the surface of a sensor may be used to capture the antigens and subsequently capture any secondary antibody specific receptors which binds to a non-competing epitope on the antigen.

Secondary antibodies that do not compete with the primary antibodies may be identified from panels of single-chain variable fragment (scFv) antibodies isolated from combinatorial naive phage display libraries or from commercial sources. Additionally, the secondary antibodies may be formulated from new scFv antibodies that are isolated from other scFv phage display libraries in the presence of high concentrations of the primary antibodies to promote the isolation of non-competing clones.

Combinatorial naive phage display libraries are another source for non-competing secondary antibodies. These libraries are typically created through the random combination of human variable light and variable heavy chain domains, resulting in the creation of antibodies that are specific for regions, i.e. epitopes, on target antigens that are not normally immunogenic. The use of phage display therefore significantly increases the areas on the antigen that can be bound by a secondary antibody.

Substrate 3 may be any microparticle, more preferably, the substrate is a microsphere, microrod, microplate and most preferably the substrate is a microsphere, microrod or microplate having a diameter of about 0.1 microns to about 100 microns. The microspheres may function like cells or spores that can be captured by a target molecule or compound attached to a sensor.

Figures 3A, 3B, 3C, 3D:
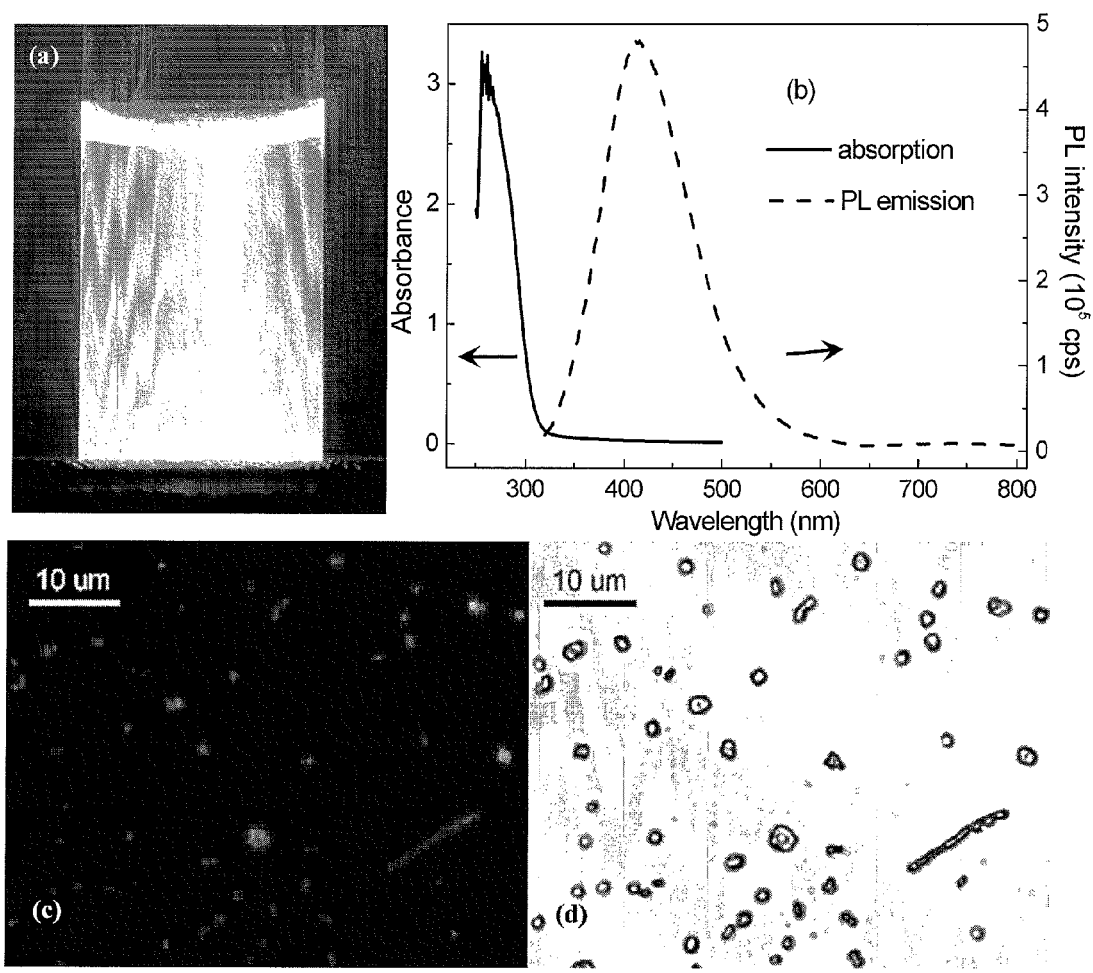
FIG. 3(a) is an image of a ZnS quantum dot suspension (pH=12, MPA:Zn:S=8:4:1, 1.6 mM) exposed to an ultraviolet lamp having a wavelength of 302 nm.
FIG. 3(b) shows an absorption and photoluminescent emission spectra of the ZnS quantum dots of FIG. 3(a).
FIG. 3(c) shows aqueous quantum dots lighting up *Salmonella t.* cells in the optical images of quantum dots-labeled *salmonella* cells under normal light.
FIG. 3(d) shows aqueous quantum dots lighting up *Salmonella t.* cells in the optical images of quantum dots-labeled *salmonella* cells under ultraviolet light.
Figure 4:
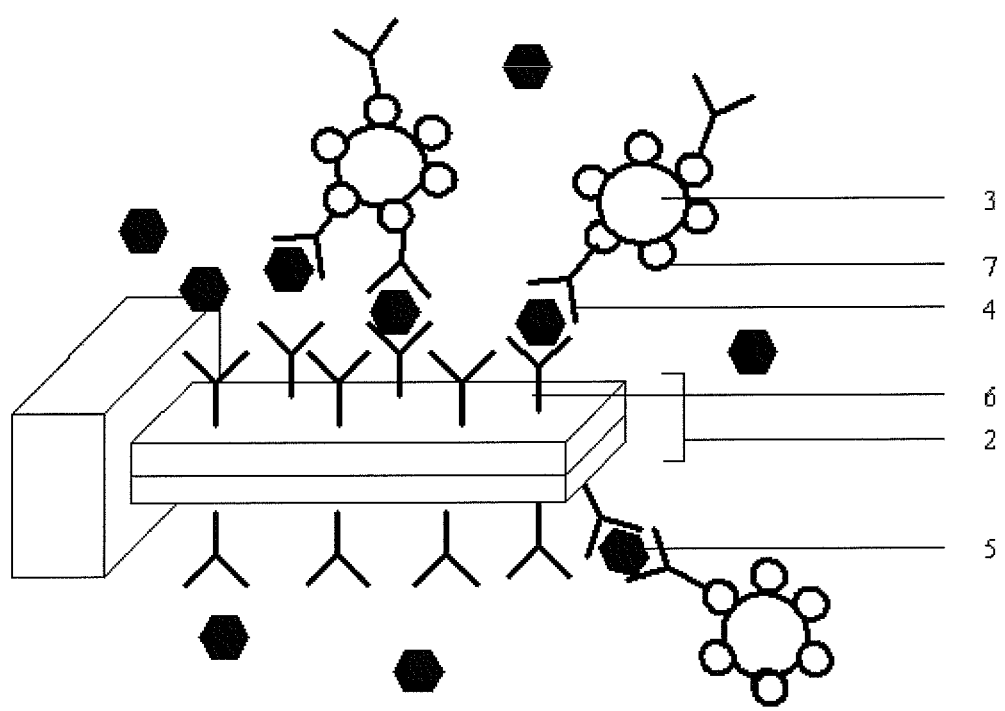
FIG. 4 shows a schematic representation of a target molecule or compound detection using a sensor coupled with target specific receptor bound substrates having quantum dots.

Optionally, substrate 3 may be populated with one or more quantum dots 7 to further enable visualization and imaging of the captured target molecules or compounds 5. Quantum dots 7 fluoresce under excitation light providing visual or fluorescent verification that the target molecules or compounds 5 are captured on the sensor 2 surface and thus confirming the presence of the target molecule or compound 5 in a sample. Therefore, it is possible to view a sample under a fluorescent microscope and determine the concentration of target molecules or compounds 5 based on the photoluminescence of the quantum dot 7 populated substrates 3. Quantum dots 7 are particularly useful in imaging proteins and cells in biological systems due to their stability against photo-bleaching and their ability to be conjugated to target proteins such as antibodies. Typically, clusters of quantum dots are able to better image biological organisms with brighter luminescence than single quantum dots 7; therefore, quantum dot 7 populated substrates 3 are expected to significantly enhance molecular imaging. FIGS. 3(c)-3(d) demonstrate the imagining of bacteria, *Salmonella t.* cells, using quantum dots directly conjugated with target specific receptor antibodies under normal light and under ultraviolet light, respectively. FIG. 3(a) shows a ZnS quantum dot suspension (MPA:Zn:S=8:4:1, 1.6 mM), having a pH=12, producing a bright blue emission after excitation using an ultraviolet lamp having a wavelength of 302 nm, and FIG. 3(b) shows the absorption and photoluminescent emission spectra of the suspension.

Quantum dots 7 may be synthesized using any standard fabrication techniques and may be of any suitable size. The environmentally friendly method for fabricating quantum dots disclosed in W. H. Shih, H. Li, M. Schillo, and W. Y. Shih, "Synthesis of Water Soluble Nanocrystalline Quantum Dots and Uses Thereof," U.S. Pat. No. 7,335,345, Feb. 26, 2008, is herein incorporated by reference. In addition, nontoxic QDs disclosed in U.S. patent application Ser. No. 11/943,790, "Synthesis of Water Soluble Nanocrystalline ZnS Quantum Dots and Uses Thereof," filed on Nov. 21, 2007, and near-infrared QDs disclosed in U.S. provisional patent application No. 61/046,899, "Water-soluble Nanocrystalline Quantum Dots Capable of Near Infrared Emissions," filed on, Apr. 22, 2008 are incorporated herein by reference. Copies of these documents are on file at the United States Patent Office at the time of filing of this International application with the United States Patent Office as the Receiving Office.

In a preferred embodiment, microsphere substrates having a diameter of about 0.1 micron-100 microns may be coated with quantum dots having a size ranging from 3 nm-100 nm.

The sensor system 1 of the present invention may be used to detect and verify the presence of a select molecule or compound 5 by exposing target specific receptor 4 bound substrates 3 to a testing environment containing the sensor 2 and sample to be tested. The target specific receptor 4 bound substrates 3 may be introduced to the testing environment or sample before, at the same time as or after the sensor 2 is exposed to the sample. In one embodiment, the sample and sensor 2 are first allowed to react for a defined period of time before the target specific receptor 4 bound substrates 3 are introduced to allow the target molecules or compounds 5 to first bind to the sensor 2. This reaction time can vary depending upon the sample size, target molecules or compounds 5 and target specific receptors 4. In another embodiment, the sample and target specific receptors 4 are first mixed to together and then exposed to the sensor 2.

Sensor system 1 functions by binding target molecules or compounds 5 that react to a first set of target specific receptors 6 immobilized on a conductive element. The binding of a target molecule or compound 5 causes a subsequent change in mass and a change in the spring constant of the sensor 2 which correspondingly shifts the mechanical resonance frequency of the sensor 2. The sensor 2 detects these shifts in resonance frequency $\Delta f$, expressed in Equation 1, which models the functionality of the sensor:

$$\Delta f_i = f_i \left( -\frac{\Delta m}{2M_e} + \frac{\Delta k}{2K_e} \right), \quad \text{(Equation 1)}$$

where $\Delta m$ and $\Delta k$ denote the mass change and the effective change in the spring constant.

Figure 5A:
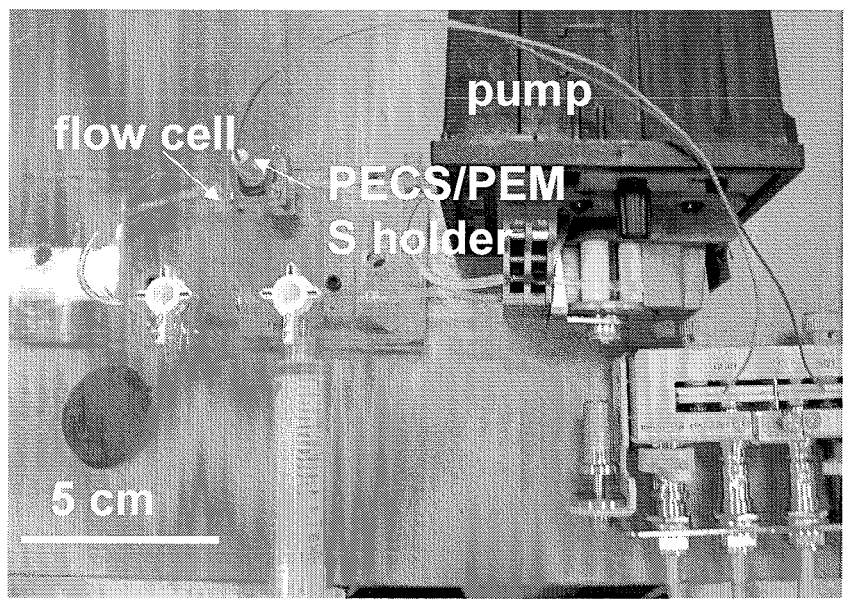
FIG. 5(a) depicts a flow cell system which can be used in conjunction with the sensor system of the present invention.
Figure 5B:
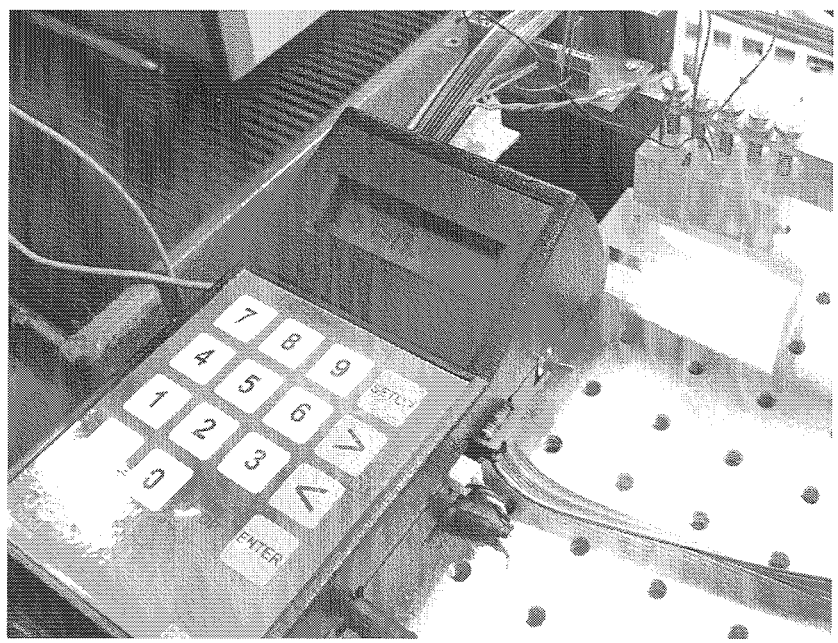
FIG. 5(b) depicts a 3.5 in by 7.5 in construct of a portable sensor system construct capable of working with 8 sensors and powered by a 9-V battery.

To further increase sensitivity and expedite the detection process, the sensor 2 may be immersed in a flowing solution for in-solution detection. The sensors are preferably situated in a flow cell system 8 to enable tailored, rapid and simultaneous detection and quantification of multiple compounds or molecules. FIG. 5(*a*) shows a flow cell system 8, with a sensor holder/measuring unit 9, having a total volume of less than 0.03-30 ml, pump 10, and a mechanism for controlling temperature and humidity (not shown). The flow cell 8 may attain flow rates of up to 0.1-100 ml/min. The total volume of the flow cell, number of channels and flow rate may vary depending upon the number of compounds to be measured. The flow cell 8 may cooperate with a portable sensor unit, shown in FIG. 5(*b*), which has multiple channels for the simultaneous quantification of multiple receptor specific molecules. The portable sensor unit is inexpensive and capable of obtaining quick measurements.

The sensor system 1 of the present application may be used in various sensing applications such as solid-liquid transition detectors, liquid viscosity and density sensors, mass sensors for in situ and in-solution detection. The sensor 2 may generally be used for detection of any molecule or compound in any sample medium but is particularly effective for in-solution detection and detection in biological samples.

The sensor system 1 may be particularly promising as a diagnostic instrument. It may be useful as a means for early detection for various forms of cancers, such as breast cancer, ovarian cancer, prostate cancer and/or other diseases, and the incorporation of quantum dots may minimize the possibility of false-positive and false-negative results. It may also be used to monitor the progress of the disease throughout treatment, and the sensor system 1 may even be incorporated in a portable device and used as a noninvasive means for testing blood and other biological samples for various pathogens, infectious agents and other markers indicative of disease in a highly sensitive and verifiable manner. For example, the sensor system 1 would enable real time protein or DNA detection with sensitivities in the range of fg/ml. Furthermore, since the system can be formulated as a cost-efficient and portable device, such a diagnostic tool may be easily incorporated in a patient's annual physical. Such a rapid direct label free detection system for pathogens or indicators such as cancer markers can be used to screen a patients' blood. Moreover, no additional chemical analysis is required, so patients will be able to rapidly obtain their results at the point of care.

Additionally, the sensor system 1 may be useful for the detection of bioterrorism agents. Primary antibody receptors specific to at least one bioterrorism agent may be bound to an electrode and secondary antibody receptors may be bound to a substrate for use in detecting the presence of bioterrorism antigens. In addition to identifying the existence of a bioterrorism agent, it may also be used to quantify the concentration of the agent.

The sensor system 1 may also be applicable for the food science and food manufacturing industry. The sensor system may be used as a diagnostic instrument for detecting pathogens or other disease agents present in food supplies and prepared or processed foods. Additionally, it may also be useful in manufacturing plants and food service industries as a means of intermittently checking food products during different phases of food preparations thereby preventing contamination and the spread of bacterial or viral diseases such as *salmonella* and *E coli*.

Sensor system 1 may also be applicable for detecting and/or measuring water-borne pathogens in water treatment plants. The sensor system may be used as an evaluation tool for monitoring the purity of drinking water or waste water.

EXAMPLES

Example 1

Figure 6:
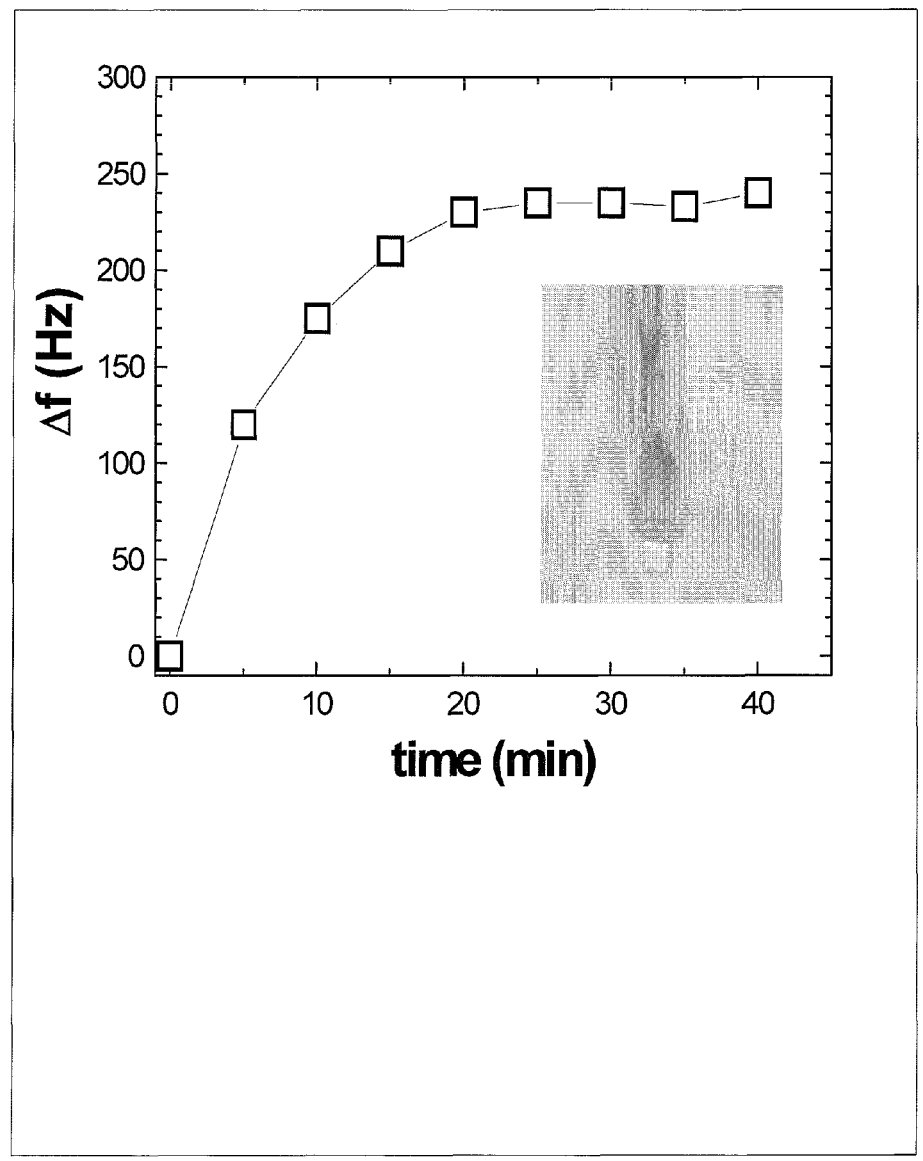
FIG. 6 is a graph of resonance frequency shift versus time of a piezoelectric microcantilever sensor in a biotinylated polystyrene suspension. The insert is a photograph of the PZT/stainless steel sensor coated with avidin.

Antigens attached to substrates are easier to detect in comparison to sensors without substrates because the additional mass of the substrates affects the detection signal of the sensor. Previous studies have established that using biotinylated polystyrene spheres to bind biotin on immobilized avidin can be easily detected whereas the same binding event using molecular biotin is more difficult. Using a PZT/stainless steel piezoelectric microcantilever having a PZT layer 1.3 mm long and 3.35 mm wide and having a 2.87 mm long gold-coated stainless steel tip coated with avidin, it was possible to bind biotin in a biotinylated polystyrene suspension. The biotinylated polystyrene spheres were approximately 2 μm in diameter and produced a resonance frequency shift of about Δf~250 Hz, as shown in FIG. 6.

By contrast, the attachment of avidin alone on the sensor surface resulted in a Δf~800 Hz (not shown). Avidin has a molecular weight of 67 KDa whereas biotin is a much smaller molecule of 244 Da. As a result, based on the mass difference, the binding of even a dense biotin layer to avidin on the surface of the cantilever would produce only a 800×(244/67000)=3 Hz shift. The results in FIG. 5 indicate that attaching the biotin to a sphere of 2 μm size enhances the detection signal of the biotin binding to avidin by a factor of 240/3=80 times. Although the factor of enhancement is less than the theoretical estimated value of $10^6$ because the sensor surface was not fully covered with the biotinylated spheres due to hindrance and/or other effects, the enhancement in detection sensitivity due to the microspheres is clearly evident.

Example 2

In one example of the sensor system of the present invention, a 1-μm size microsphere has roughly $4\times10^4$ quantum dots on its surface and can amplify the optical signal of a QD-marker protein binding $4\times10^4$ fold. Moreover, since a 1-μm size microsphere has a mass $8\times10^6$ times that of a quantum dot, the binding of a microsphere can enhance the piezoelectric microcantilever sensor resonance frequency shift by $8\times10^6$ times that which is achievable with a single quantum dot. As a result, quantum dot coated-microspheres, not only can image but also enhance detection sensitivity.

Example 3

Figure 7:
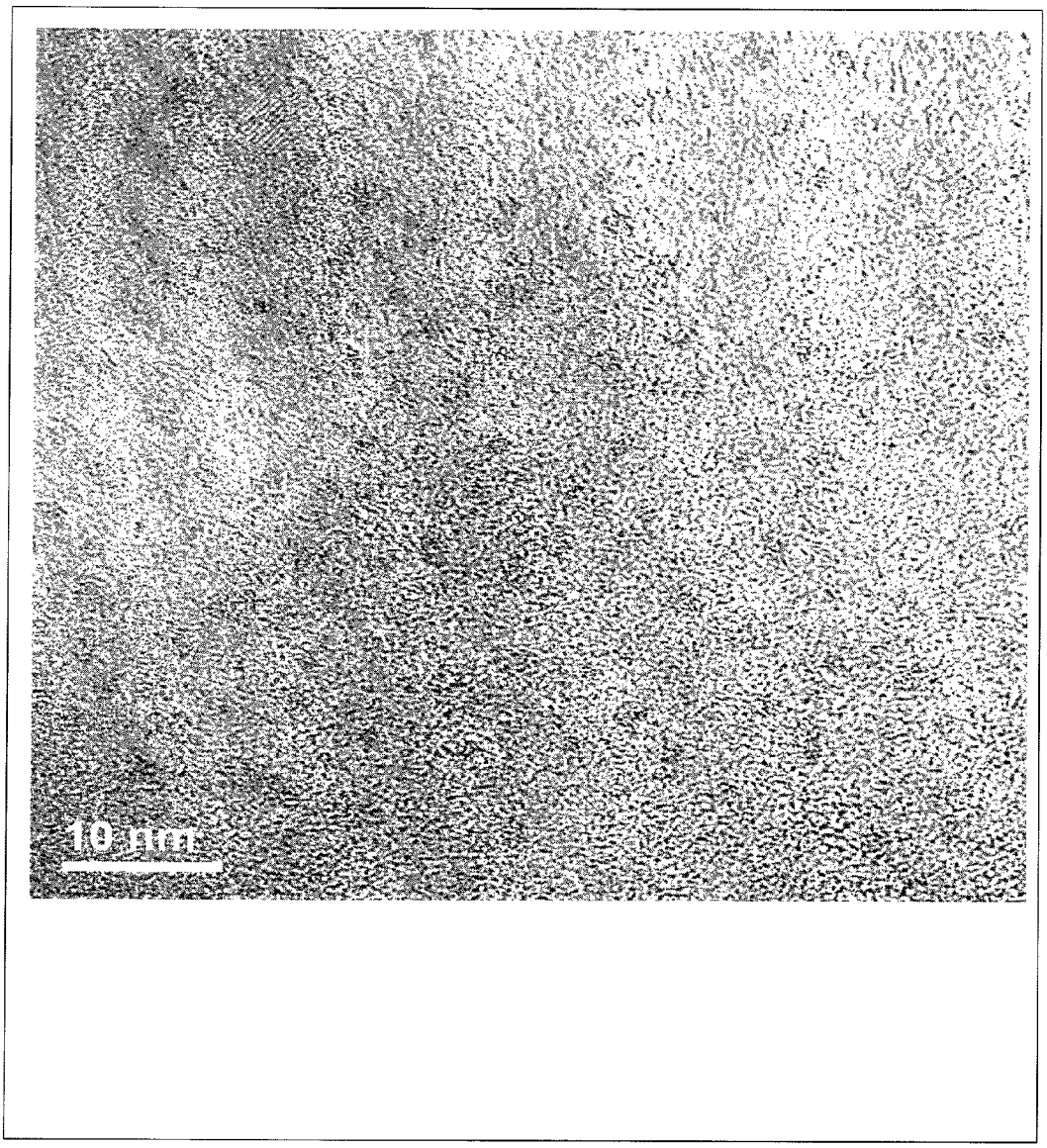
FIG. 7 is a transmission electron microscope image of ZnS quantum dots synthesized with MPS capping molecules.

In one preferred embodiment, the sensor system comprises antigen-coated microspheres decorated with metal sulfide (MS) quantum dots. The MS quantum dots may be fabricated from various materials using various different fabrication means. MS quantum dots were be synthesized using 3-mercaptopropionic acid (MPA), metal nitrate $(M(NO_3)_2)$ and sodium sulfide $(Na_2S)$. The well-dispersed transparent and highly photoluminescent MS quantum dots, which may be fabricated in 30 minutes at room temperature, produced a MPA/M ratio of about 8:2. Replacing $M(NO_3)_2$ with zinc nitrate $[Zn(NO_3)_2]$ and, ZnS quantum dots were fabricated at 100° C. and at a pH=9 in a hydrothermal bomb. The resultant ZnS quantum dots were found to be highly luminescent. The highly photoluminescent ZnS quantum dots of FIGS. 3(c)-3(d) were synthesized at room temperature in 30 min by adjusting the synthesis solution pH to 12. To improve the ambient stability of the quantum dots, MPA were replaced with 3-mercaptopropyl trimethoxysilane (MPS). As shown in FIG. 7, the MPS-capped ZnS quantum dots are monodispersed. The photoluminescent intensity of MPS-capped ZnS increased over time, regardless of whether it was placed in the dark or exposed to day light; samples stored at room temperature displayed stronger emission than that stored at 4° C. These results indicate that the MPS-capped ZnS quantum dots can be handled under ambient condition without refrigeration. The ambient stability of MPS-ZnS has the major advantage that they can be further modified for a variety of applications without their loss of photoluminescent properties.

Figure 8:
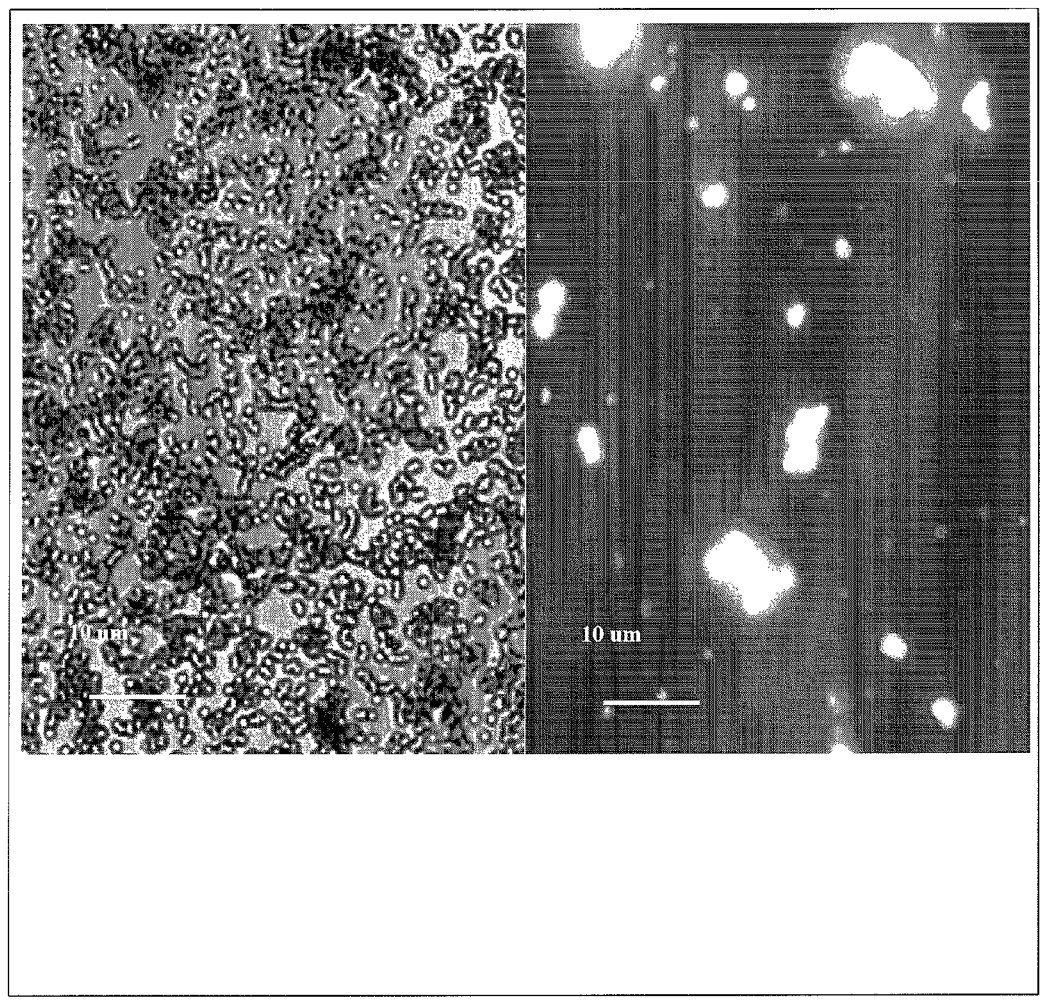
FIG. 8(a) is an optical micrograph of CdS quantum dots attached to microbeads in normal light.
FIG. 8(b) is an optical micrograph of CdS quantum dots attached to microbeads in ultraviolet light.

MPA-capped quantum dots were previously used to bind amine-modified 1 μm in diameter polystyrene spheres through peptide bonds. The carboxyl group of MPA on the CdS quantum dots surface was first activated by 1-ethyl-3-(3-dimethylaminopropyl) carbodiimide (EDC) and N-hydrocylsulfo-succinimide (sulfo-NHS). The spheres with amine groups were added to the activated quantum dot suspension. After incubation, rinsing and centrifuging the mixture and after removing the supernatant, which contained the unbound quantum dots and other chemicals, the precipitate was collected and the suspensions were examined under the fluorescence microscope, as shown in FIGS. 8(a)-8(b). FIG. 8(a) is an optical micrograph of CdS quantum dots attached to microbeads in normal light. FIG. 8(b) is an optical micrograph of CdS quantum dots attached to microbeads in UV light. Clusters of microbeads contain aggregates of quantum dots giving brighter image under UV light.

For more stable MPS-capped quantum dots, there are several approaches to fabricate the quantum dots decorated and antibody coated microspheres. In one approach avidin-conjugated quantum dots were first synthesized using SMCC (sulfosuccinimidyl-4-(N-maleimidomethyl)cyclohexane-1-carboxylate) as linker to bind MPS-capped quantum dots to avidin. The avidin-conjugated quantum dots were then coated on biotinylated polystyrene spheres. The number ratio between the quantum dots and polystyrene and their concentrations were varied in order to achieve dispersed antibody coated quantum dot microsphere suspensions.

Another approach involved spheres with amine surface groups where SMCC was added to the polystyrene suspension to facilitate the NHS ester to react with primary amines. After purifying the mixture to remove the excess SMCC by rinsing and centrifugation, the precipitated polystyrene spheres were collected and mixed with MPS-capped quantum dots.

A third approach involves spheres with carboxyl groups on their surface wherein sodium silicate was added to the MPS-capped quantum dot suspension to form a silica layer. The silica-coated quantum dots were then reacted with aminopropylsilane (APS) to modify the surface with primary amine groups. The reaction between amine and carboxyl groups resulted in the formation of quantum dot decorated and antibody coated microspheres. The conjugation of secondary antibody to microspheres utilizes the same surface chemistry employed in the immobilization of the primary antibody on the surface of sensor as described in Example 4.

Example 4

It is envisioned that the sensor system of the present invention may be particularly useful for diagnosing breast cancer from a patient's blood sample. Because the sensor system of the present invention improves sensitivity by several orders of magnitude and is capable of verifying the detection results, it may be possible to more successfully and more accurately detect breast cancer at an early stage when treatment is most effective. A sensor system for breast cancer detection is envisioned to comprise a piezoelectric microcantilever sensor (PEMS) having a primary antibody coating and polystyrene spheres decorated with quantum dots (Q-spheres) Secondary antibodies will then be immobilized on the surface of the Q-spheres to bind to the breast cancer markers.

One of the most promising biomarkers for identifying breast cancer is HER-2, a member of the epidermal growth factor receptor family. 20-40% of breast cancers are HER-2 positive and over-expression of this receptor is correlated with a poor prognosis. As no single specific breast cancer antigen has been found to date that is capable of identifying all breast cancer cases, a panel of antibodies will be used which is expected to achieve at least a 95% detection rate for breast cancer. The panel of anti-HER-2 scFv molecules will be isolated from two naïve human scFv phage display libraries. These scFv molecules are composed of variable light and variable heavy chains of antibody molecules, thereby duplicating an antibody's antigen binding pocket. These scFv molecules are readily expressed from *E. coli* and can be modified e.g., with carboxy-terminal residues to facilitate site-specific coupling to a piezoelectric microcantilever sensor. The relatively small size of the secondary antibody coated microspheres, about 25 kDa, facilitates a dense distribution on a piezoelectric microcantilever surface. Panels of scFv molecules specific for a variety of human breast cancer antigens including, HER-2, HER3, HER4, EGFR and the Mullerian Inhibiting Substance Type II receptor (MISIIR) have already been isolated and thus may provide suitable candidates for the present invention. Additional panels of scFv specific for additional breast cancer antigens, e.g. CA-125, CEA, CEA15.3 etc., may be isolated as the experiment progresses. Milligram quantities of recombinant HER-2 extracellular domain (ECD) for use in the selection of scFv molecules and in the development of the assay system may also be expressed.

Initial studies targeting HER-2 will use anti-HER-2 scFv molecules (H3). This scFv has been previously successful in detecting nanogram quantities of recombinant HER-2 from solutions containing one milligram per milliliter of serum albumin (from 1/40 serum). Secondary scFv and IgG candidates for conjugation to the Q-spheres that do not block binding of H3 to HER-2 will then be identified. The secondary antibody candidates will be conjugated to the Q-spheres and then re-assayed so as to enable binding to the H3-HER-2 ECD complex. The candidate antibody that generates the greatest signal will be selected as the secondary antibody. Upon isolating and selecting the appropriate secondary antibody, the effectiveness of the sensor system to detect HER-2 will be tested by comparing the detection sensitivity of a PEMS to that of a system including a PEMS and secondary antibody bound Q-spheres.

Figure 9:
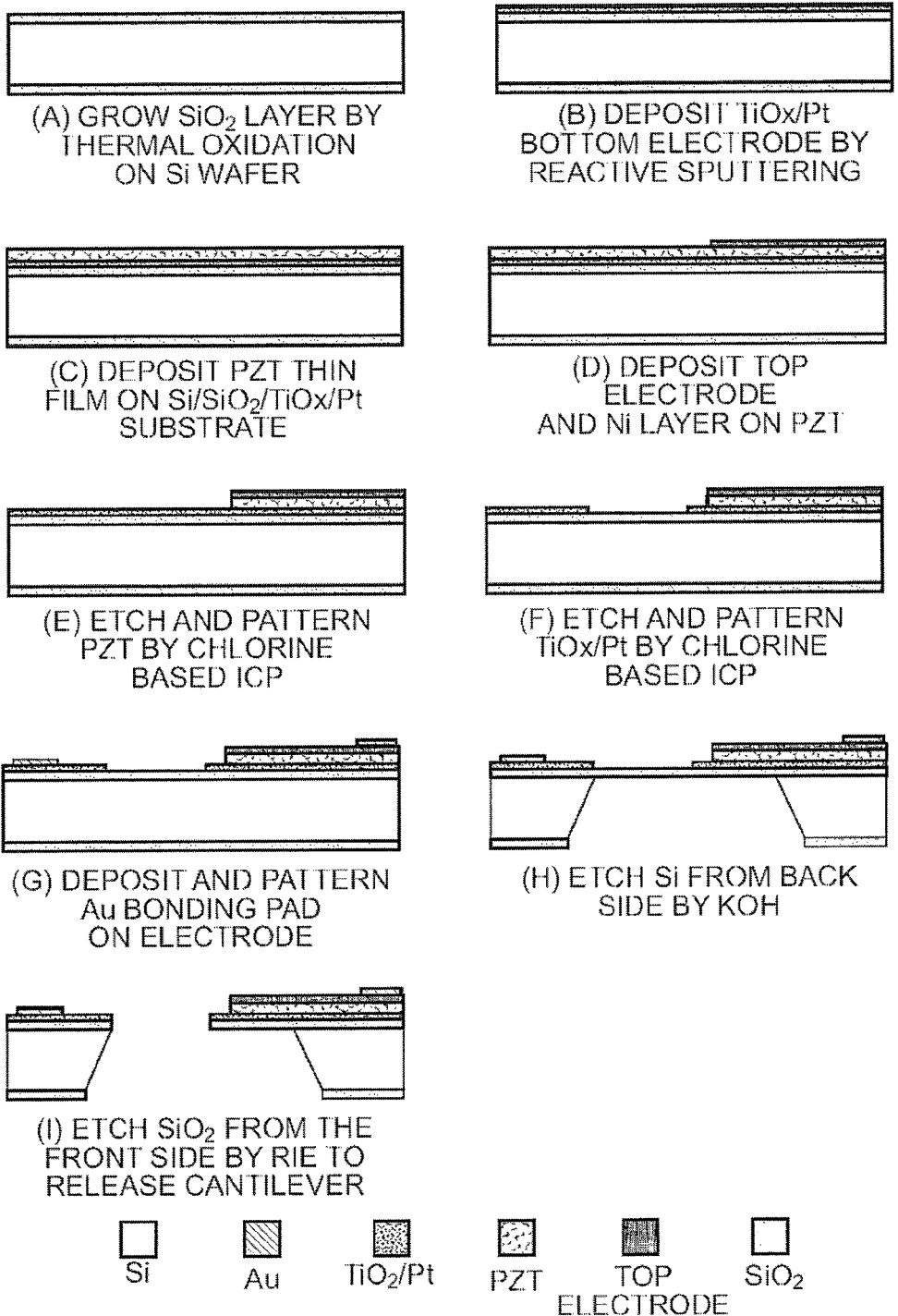
FIGS. 9(a)-(i) depict a schematic representation of a method for fabricating PZT/SiO2 piezoelectric microcantilever sensors.

The PEMS of the sensor system will be fabricated by two approaches. In one approach a PZT/SiO$_2$ system is fabricated according to the method shown in FIG. 9. Z. Shen, W. Y. Shih, and W.-H. Shih, "Self-Exciting, Self-Sensing PZT/SiO$_2$ Piezoelectric Microcantilever Sensors with Femtogram/Hz Sensitivity," *Appl. Phys Lett.*, 89, 023506 (2006). Another approach involves the formation of lead magnesium niobate-lead titanate (PMN-PT) freestanding films followed by electroplating and wire-saw cutting. J. A. Capobianco, W. Y. Shih, and W.-H. Shih, "Methyltrimethoxysilane-Insulated Piezoelectric Microcantilevers for Direct, All-Electrical Biodetection in Buffered Aqueous Solutions," *Rev. Sci. Instru.*, 77, 125105 (2006). The experiment will also explore the use of laser cutting to fabricate PEMS of smaller dimensions. PEMS detection of cancer markers will be verified by imaging the antigens using Q-spheres that have been conjugated with the secondary antibodies.

At a later stage, the sensor system of the present invention, including the antibody coated Q-spheres, will be used to detect the presence and concentration of HER-2 in serum. After detection, a fluorescence microscope will be used to image the photoluminescence of the Q-spheres. Q-spheres that have been conjugated with secondary antibody will be first mixed with a serum that contains the HER-2 antigen. PEMS will then be immersed in the Q-spheres-antigen serum. The resonance frequency of PEMS will be monitored to study the enhancement effect due to the Q-spheres. While not wishing to be bound by theory, it is expected that the antigens will bind with the Q-spheres in solution and then the antigen Q-sphere complex will bind to the PEMS. These results will be compared with the results of the above-mentioned same PEMS, having no secondary antibody coated Q-spheres, in the same serum. Additionally, to eliminate the nonspecific binding events, the same detection with the same serum without the antigens will be performed. The difference in frequency change between the sample with antigen and that without antigen will provide the specific detection of antigens.

Comparative Example A & Example 5

The ability of a PEMS coated with microspheres and a PEMS having no microspheres to detect HER-2 in low concentration solutions was investigated.

In comparative example A, a PEMS was coated with scFv specific for HER-2 was tested. Sulfo-SMCC was used as a linker for antibody immobilization. To effectively bind SMCC to scFv, 5 mM SMCC was mixed with 400 nM scFv for 2 hours. The unreacted SMCC was removed by 4 repetitions of microcentrifugation with a 10 kDa filter. The MPS-coated PEMS was then soaked in the scFv-bound SMCC solution. The sulfhydryl of the MPS on the sensor surface reacted with the maleimide of the scFv-bound SMCC to immobilize the scFv.

In this experiment, a biotin-avidin-biotin sandwich scheme was used to immobilize the scFv. First, MPS was coated on the surface of the PEMS by first soaking the PMN-PT/Cu PEMS in a 0.1 mM solution of MPS in ethanol for 30 min then in a 40 mM solution of MPS in ethanol titrated to pH 4.5 by acetic acid for 2 hours. Biotin was then attached to the sulfhydryl on the MPS by maleimide-activated biotin (Pierce). The maleimide was separated from the biotin by polyethylene glycol (PEG). The MPS-coated PEMS was soaked in a 5 mM (2.6 mg/ml) maleimide activated biotin solution in PBS for 2 hours and rinsed well with PBS to remove any excess biotin. The cantilever was then soaked in a 4 mg/ml avidin solution. Next, the scFv was then biotinylated with NHS-Biotin (Pierce). A 15 molar fold excess of the scFv (1 µM) was prepared and allowed to react at 4° C. for 3 hr. The excess biotin was then removed by microcentrifugation using a 10 k filter (Millipore) at 4000 RPM for 10 min. The retentate was then mixed with PBS and microcentrifuged again. The process was repeated 3 times. After the second spin the centrifuge began to warm up. The tubes were placed in the refrigerator and the final centrifugation was performed when the machine cooled to room temperature. The scFv was then immobilized on the PEMS surface by dipping the avidin-coated PEMS in the biotinylated scFv solution. To block nonspecific binding, the scFv-immobilized PEMS was soaked in a 3% Bovine Serum Albumin (BSA) solution prepared in PBS. After blocking, the PEMS was rinsed in a solution with 1% BSA and 0.1% TWEEN20. After rinsing and in between trials the PEMS was submerged in a diluted fetal bovine serum (serum/PBS 1/40).

Figure 10:
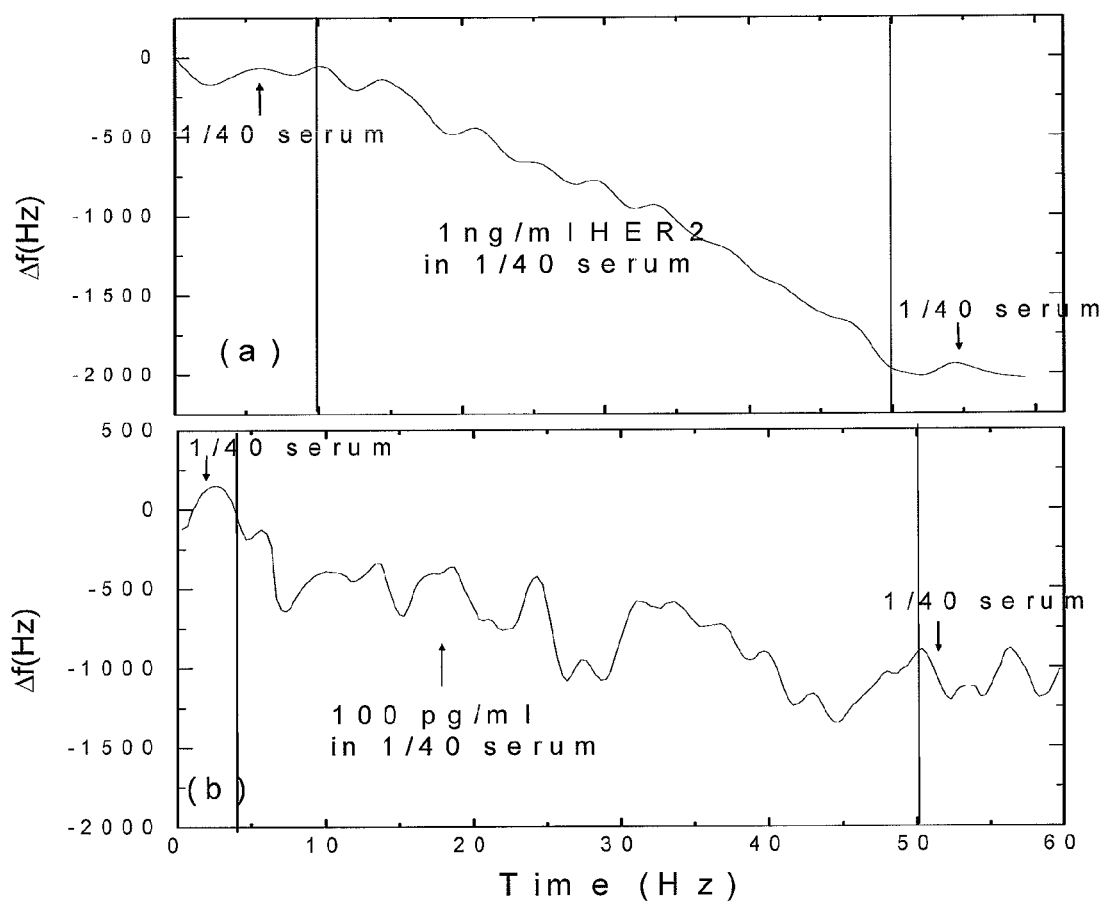
FIG. 10(a) is a graph of resonance frequency shift as a function of time of a PMN-PT PEMS in 1 ng/ml of HER-2.
FIG. 10(b) is a graph of resonance frequency shift as a function of time of a PMN-PT PEMS in 100 pg/ml of HER-2 in 1/40 diluted serum.

FIGS. 10(*a*)-(*b*) show the detection results of HER-2 in the 1/40 diluted fetal bovine serum using a PMN-PT PEMS. In particular, the resonance frequency shift versus time in 1 ng/ml and 100 pg/ml of HER-2 in 1/40 diluted fetal bovine serum are shown in FIG. 10(*a*) and FIG. 10(*b*), respectively. As can be seen, the detection in 1 ng/ml of HER-2 yielded −2000 Hz frequency shift and that in 100 pg/ml HER-2 in diluted serum yielded −700 Hz frequency shift. The PMN-PT PEMS was 600 µm long, 370 µm wide consisting of an 8 µm thick PMN-PT film and a 3 µm thick copper layer and exhibited $4 \times 10^{-13}$ g/Hz mass detection sensitivity. The concentration sensitivity of 100 pg/ml was outstanding because of the better immobilization and better blocking scheme. In a comparative study, the biotin-avidin-biotin immobilization scheme packed more than twice the number of scFv on the sensor surface and consequently bound more than twice as many HER-2 as other schemes that we have tried. The better scFv immobilization also made blocking of the non-specific binding more effective, thus enabling the detection of HER-2 at a lower concentration.

By comparison, PEMS designed to bind microspheres specific for HER-2 (Example 5) were also found to be effective for binding HER-2. Two PZT/glass PEMS are used to demonstrate the ability of selectively binding polystyrene microspheres which have been coated with an antibody specific for HER-2. The PEMS was first insulated with MPS (Sigma, St. Louis, Mo.) using a solution method. First, the cantilevers' glass tip was submerged in a piranha solution (two parts of 98% sulfuric acid (Fisher, Fair Lawn, N.J.) with one part of 30% hydrogen peroxide (FisherBiotech, Fair Lawn, N.J.)) at 20° C. for 20 minutes to clean the glass surface. The cantilever tip was rinsed with deionized water and then with ethanol. The cantilevers were then totally submerged in a 1% MPS solution in ethanol titrated to a pH of 4.5 using acetic acid. The cantilevers were allowed to soak for a total of twelve hours.

The glass tips were then immobilized with different receptors. One cantilever was coated with anti-*E. coli* (Kirkegaard & Perry Laboratory, Gaithersburg, Md.) and the other was coated with an anti-HER-2 single chain variable fragment (scFv). The immobilization of these receptors was carried out under identical conditions using a heterobifunctional cross linker Sulfosuccinimidyl-4-N-maleimidomethyl cyclohexane-1-carboxylate sulfo-SMCC (Pierce). A 2.8 µM solution of receptor was activated with 50 molar fold excess SMCC for 1.5 hours at 4° C. Next the excess\unreacted SMCC was removed through centrifugation using a 10K filtered centrifuge tube. The filtered retentate was then added to a conjugation buffer containing 5 mM EDTA. The MPS coated cantilever was first soaked in 5 mM EDTA in DI water for 20 minutes, and then it was soaked in the activated receptor solution. EDTA functioned to chelate divalent metals, thereby reducing disulfide formation.

Carboxylic acid terminated polystyrene beads were conjugated with Herceptin using carbodiimide chemistry. A stock solution containing $10^9$ beads/ml was used. Each bead has an approximate area of $5\times10^{-11}$ m$^2$. The approximate area of each NHS molecule is $8\times10^{-19}$ m$^2$, as a result, $6\times10^{15}$ molecules were needed. This requirement was sufficiently met by using 3 mM NHS and 5 mM EDC in an MES buffer for 25 minutes at room temperature. The excess/unreacted NHS-EDC was removed using a 300 K centrifugation filter. After activation the beads were mixed with Herceptin. The approximate area of each Herceptin molecule is $8\times10^{-17}$ m$^2$. As a result, $6\times10^{14}$ antibodies were needed to coat the surface of all the beads. A 100-fold excess of Herceptin was used. The activated bead-Hercetpin solution was allowed to react for 2 hours at 4° C. Afterward the unbound Herceptin was removed using a 300 K centrifuge filter.

Figure 11A:
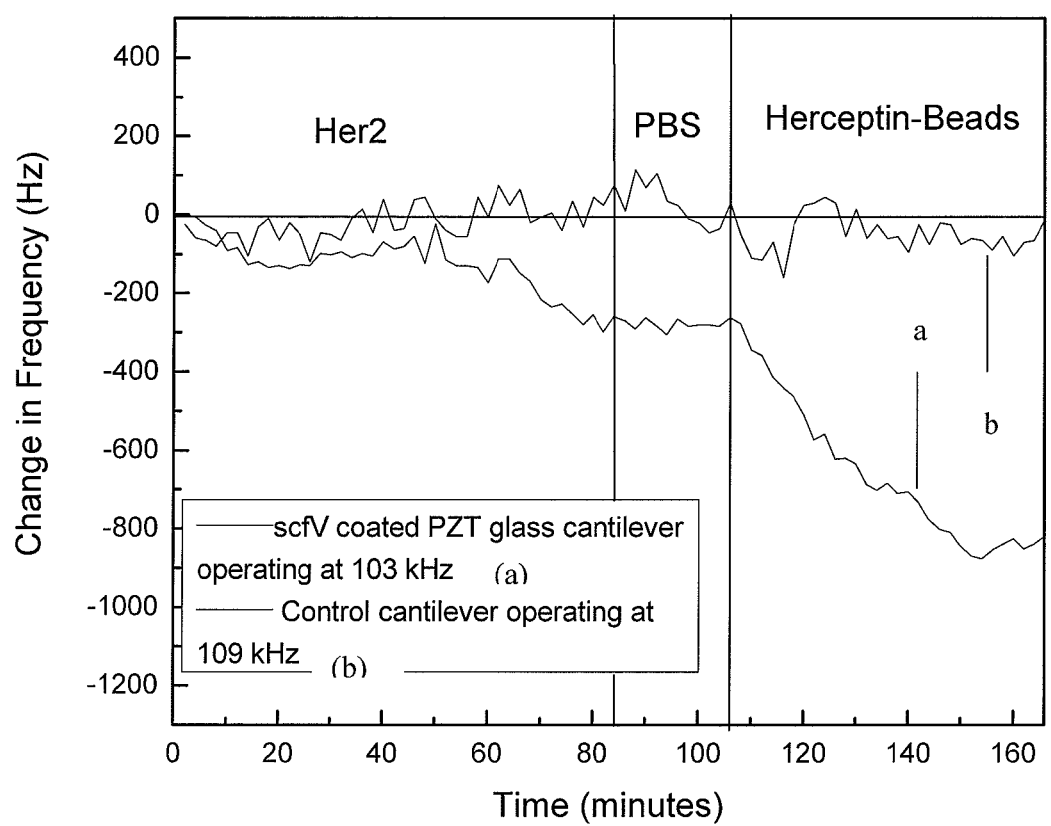
FIG. 11(a) is a graph of resonance frequency shift as a function of time for a cantilever coated with an scFv selective for HER-2 (a) and a cantilever coated with an antibody for *E. coli* (b) when exposed to a 0.86 mg/ml solution of HER-2, a rinse in PBS and herceptin coated polystyrene beads.
Figure 11B:
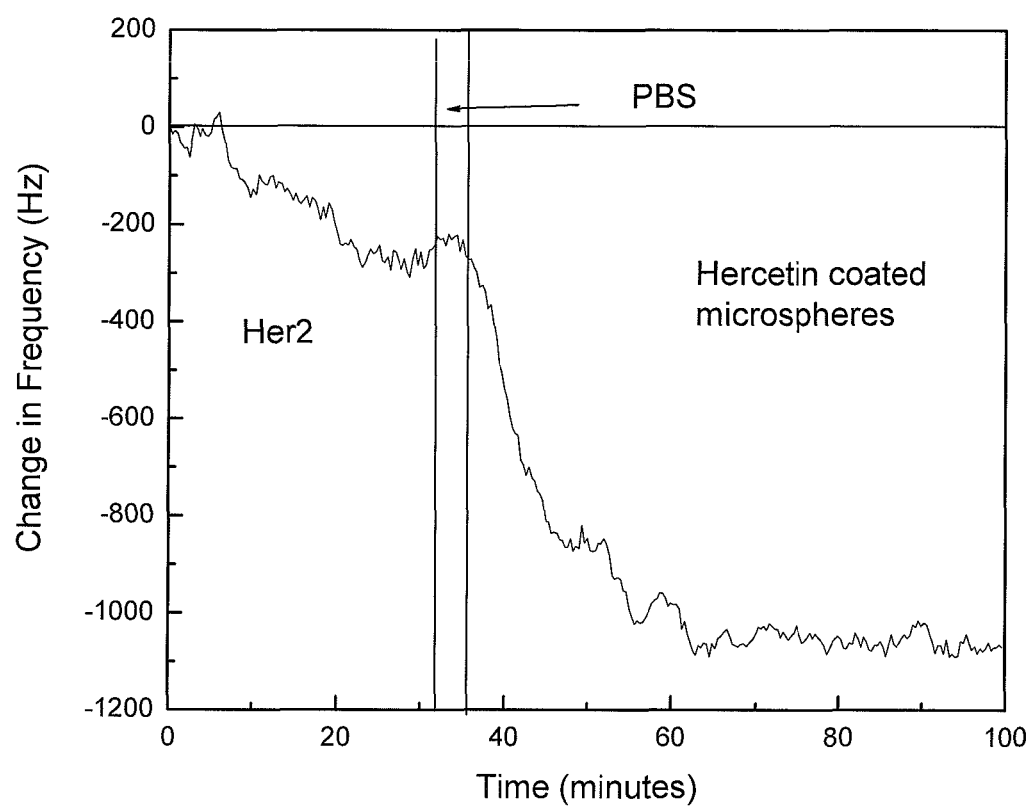
FIG. 11(b) is a graph of resonance frequency shift as a function of time for a cantilever coated with an scFv selective for HER-2 when exposed to HER-2, a PBS rinse and herceptin coated polystyrene beads.

After immobilization the cantilevers were rinsed with PBS and then placed in the same 3.5 ml home built flow cell containing an 86 µg/ml solution of HER-2 ECD. The solution was flowed parallel to the face of the cantilever at a rate of 0.7 ml/minute. The results of this experiment are depicted in FIG. 11(*a*). After 85 minutes the cantilever with the anti-HER-2 scFv responded by shifting 300 Hz, and the control cantilever did not change from its resonant frequency. The control cantilever was coated with an anti-Salmonella antibody. Following the exposure to HER-2 the flow cell was rinsed with PBS, which was circulated through the flow cell for 20 minutes to rinse the cantilever surface. Following the rinse polystyrene microbeads conjugated with Herceptin with bead concentration of $10^7$/ml were added to the flow cell and recirculated for 60 minutes, which caused a shift in resonant frequency of 600 Hz in the scFv coated cantilever, while the control cantilever did not respond. While the resonance frequency shift due to the Herceptin beads was higher than that of the HER-2 detection it is not as high as expected, possibly due to cross-reactivity between scFv and Herceptin as was seen, for example, in FIG. 11(*a*).

Herceptin beads detection was carried out using sensors with HER-2 immobilized on the surface. To immobilize HER-2 on the sensor surface, HER-2 was first activated in PBS with sulfo-SMCC. An 88 µg/ml solution of HER-2 was activated with a 50 fold molar excess of SMCC for 1.5 hours at 4° C. Next the excess\unreacted SMCC was removed through centrifugation using a 10 K filtered centrifuge tube. The filtered retentate was then added to a conjugation buffer containing 5 mM EDTA. The MPS coated cantilever was first soaked in 5 mM EDTA in DI water for 20 minutes, and then it was soaked in the activated HER-2 solution for immobilization.

FIG. 11(*b*) shows the resonance frequency shift due to binding of the HER-2 to the cantilever surface and then that from the binding of Herceptin beads to the HER-2 coated surface. As can be seen, similar to the result shown in FIG. 11(*a*), the resonance frequency shift from binding of the HER-2 to the sensor surface resulted in about a 250 Hz shift. The resonance frequency shift due to the binding of the Herceptin beads was about 900 Hz, about twice what was observed in FIG. 11(*a*), supporting the notion that it may be the cross reactivity that limited the binding of the beads in the previous example.

It is to be understood, however, that even though numerous characteristics and advantages of the present invention have been set forth in the foregoing description, together with details of the structure and function of the invention, the disclosure is illustrative only, and changes may be made in detail, especially in matters of shape, size and arrangement of parts within the principles of the invention to the full extent indicated by the broad general meaning of the terms in which the appended claims are expressed.

The invention claimed is:

1. A sensor system comprising:
   at least one sensor including a plurality of target specific receptors capable of binding a specific target molecule or compound,
   a detector operatively associated with said sensor and being capable of detecting a change in at least one property of said sensor;
   substrates positioned to contact said at least one sensor, each said substrate having at least one target specific receptor directly or indirectly bound to said substrate, said target specific receptor being capable of binding said target molecule or compound; and
   quantum dots bound to said substrates;
   wherein said target specific receptors bound to said substrates do not bind to the same binding site on said target molecule or compound as said target specific receptors of said sensor.

2. The sensor system of claim 1, wherein said target specific receptors are bound to said quantum dots.

3. The sensor system of claim 1, wherein said sensor is a piezoelectric microcantilever sensor.

4. The sensor system of claim 3, wherein said property of said sensor is a resonance frequency.

5. The sensor system of claim 1, wherein each said substrate has at least one target specific receptor bound thereto.

6. The sensor system of claim 1, wherein said substrates are selected from the group consisting of microparticles, microbeads, microrods, microplates, and microspheres.

7. The sensor system of claim 6, wherein said substrates have a diameter of about 0.1 micron to about 100 micron and are selected from the group consisting of: microspheres, microrods and microplates.

8. A method for determining a presence or concentration of a target molecule or compound in a sample using the sensor system of claim 1, said method comprising the steps of:
   binding said target molecule or compound in the sample to at least one said substrate having at least one target specific receptor for binding said target molecule or compound to said substrate; subsequently exposing the sensor system of claim 1 to the sample including the at least one substrate bound to said target molecule or compound;
   detecting a change in at least one property of said sensor;
   determining a presence or concentration of a specific target molecule or compound in the sample from said detected change in at least one property of said sensor; and
   validating the presence of the target molecule or compound by observing photoluminescence of said quantum dots.

9. The method of claim 8, wherein exposing a sensor system to the test sample comprises the steps of:
   binding to said sensor, said at least one substrates bound to said target molecule or compound;
   detecting a force exerted on said sensor or a resonance frequency shift of said sensor by said bound target molecule or compound and said substrate.

10. The method of claim 8, wherein said sensor is immersed in a solution comprising said at least one substrate bound to said target molecule or compound.

* * * * *